Figure 1:
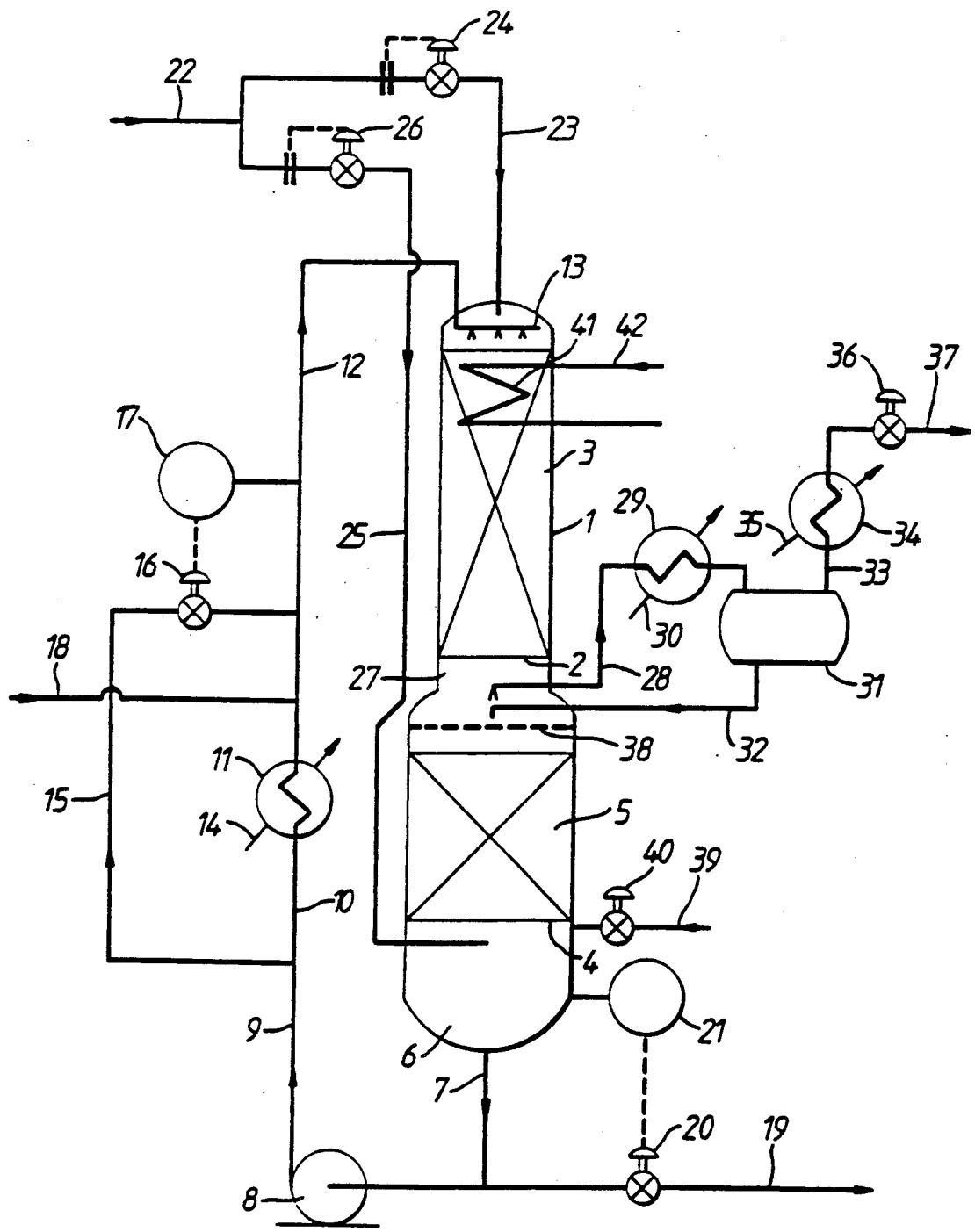

United States Patent [19]

Harrison et al.

[11] Patent Number: 5,093,535
[45] Date of Patent: Mar. 3, 1992

[54] CATALYTIC HYDROGENATION PROCESS

[75] Inventors: George E. Harrison, Essex; Alan J. Dennis, Cleveland, both of England

[73] Assignee: Davy McKee (London) Limited, London, England

[21] Appl. No.: 476,453

[22] PCT Filed: Nov. 25, 1988

[86] PCT No.: PCT/GB88/01027
§ 371 Date: Jun. 4, 1990
§ 102(e) Date: Jun. 4, 1990

[87] PCT Pub. No.: WO89/05286
PCT Pub. Date: Jun. 15, 1989

[30] Foreign Application Priority Data

Dec. 2, 1987 [GB] United Kingdom ............... 8728156

[51] Int. Cl.$^5$ .................. C07C 29/141; C07C 29/145; C07C 29/149; C07C 5/10
[52] U.S. Cl. .................................. 568/881; 260/409; 260/413; 564/420; 508/835; 508/861; 508/863; 585/266
[58] Field of Search ............... 568/881, 835, 861, 863; 564/420; 260/409, 413 R; 585/266

[56] References Cited

U.S. PATENT DOCUMENTS

| | | | |
|---|---|---|---|
| 3,880,940 | 9/1975 | Baer et al. | 568/881 |
| 4,288,640 | 9/1981 | Schuster et al. | 568/874 |
| 4,451,677 | 5/1984 | Bradley et al. | 568/881 |
| 4,510,092 | 4/1985 | Rosen | 260/409 |
| 4,626,604 | 12/1986 | Hiles et al. | 568/835 |
| 4,960,960 | 10/1990 | Harrison et al. | 568/881 |

FOREIGN PATENT DOCUMENTS 1002372  8/1965  United Kingdom ............... 568/881
1362071  7/1974  United Kingdom .

Primary Examiner—J. E. Evans
Attorney, Agent, or Firm—Rothwell, Figg, Ernst & Kurz

[57] ABSTRACT

A liquid phase catalytic hydrogenation process is described in which an organic feedstock, such as an aldehyde containing from 2 to about 20 carbon atoms, is contracted with hydrogen in the presence of a solid hydrogenation catalyst under hydrogenation conditions to produce a hydrogenation product, such as the corresponding alcohol containing from 2 to about 20 carbon atoms, which process comprises passing a feed solution of the organic feedstock in an inert diluent therefor downwardly in co-current with a hydrogen-containing gas through a hydrogenation zone containing a bed of a particulate hydrogenation catalyst whose particles substantially all lie in the range of from about 1.5 mm to about 5 mm, maintaining the bed of catalyst particles under temperature and pressure conditions conducive to hydrogenation, recovering from a bottom part of the bed a liquid phase containing the hydrogenation product, controlling the rate of supply of the feed solution to the bed so as to maintain a superficial liquid velocity of the liquid down the bed in the range of from about 1.5 cm/sec to about 5 cm/sec, and controlling the rate of supply of the hydrogen-containing gas to the bed so as to maintain at the top surface of the bed of catalyst particles a flow of hydrogen-containing gas containing from 1.00 to about 1.15 times the stoichiometric quantity of hydrogen theoretically necessary to convert the organic feedstock completely to the hydrogenation product.

23 Claims, 10 Drawing Sheets

CATALYTIC HYDROGENATION PROCESS

This invention relates to a liquid phase catalytic hydrogenation process.

Heterogeneous catalytic hydrogenation processes of various kinds are widely practised on a commercial scale and are used for hydrogenation of a wide variety of organic feedstocks. Typically such hydrogenation reactions are conducted at a pressure of from about 1 bar to about 300 bar and at a temperature in the range of from about 40° C. to about 380° C. Examples include hydrogenation of aldehydes to alcohols, of unsaturated hydrocarbons to saturated hydrocarbons, of acetylene-derived chemicals to saturated materials, of unsaturated fatty acids to saturated fatty acids, of ketones to secondary alcohols, of esters of unsaturated fatty acids to esters of partially or fully hydrogenated fatty acids, of nitriles to primary amines, and of certain sugars to polyhydroxyalcohols. Also worthy of mention is the hydrogenation of quinones, for example the hydrogenation of 2-ethylanthraquinone as a step in the production of hydrogen peroxide. This cyclohexanol is produced commercially by catalytic hydrogenation of cyclohexanone, and iso-propanol by catalytic hydrogenation of acetone. An example of hydrogenation of an unsaturated hydrocarbon is the production of cyclohexane from benzene. Typical catalysts for such hydrogenation reactions include Group VIII metal catalysts, such as nickel, palladium and platinum. Production of butane-1,4-diol by hydrogenation of but-2-yn-1,4-diol is an example of hydrogenation of an acetylene-derived chemical. A suitable catalyst for this reaction has been described as a granular nickel-copper-manganese on silica gel. The production of stearic acid by catalytic hydrogenation of the corresponding unsaturated acids, linoleic acid and linolenic acid, at a temperature of about 150° C. and at a pressure of about 14.75 bar to about 32 bar and using a nickel, cobalt, platinum, palladium, chromium or copper/zinc catalyst, is an example of the hydrogenation of unsaturated fatty acids to yield saturated fatty acids. So-called "hardening" of vegetable oils is an example of hydrogenation of esters of unsaturated fatty acids. Production of beta-phenylethylamine by hydrogenation of benzyl cyanide is an example of hydrogenation of a nitrile. As examples of hydrogenation of sugars to polyhydroxyalcohols there can be mentioned hydrogenation of ketose and aldose sugars to hexahydroxyalcohols, for example hydrogenation of D-glucose to sorbitol and of D-mannose to mannitol.

An important route to $C_3$ and higher alkanols involves hydroformylation of alpha-olefins, such as ethylene, propylene, and butene-1, to yield the corresponding aldehyde having one more carbon atom than the starting olefin. Thus ethylene yields propionaldehyde and propylene yields a mixture of n- and iso-butyraldehyde (with the n-isomer usually predominating). These aldehydes yield the corresponding alkanols, e.g. n-propanol and n-butanol, upon catalytic hydrogenation. The important plasticiser alcohol, 2-ethylhexanol, is made by alkali-catalysed condensation of n-butyraldehyde to yield the unsaturated aldehyde, 2-ethyl-hex-2-enal, which is then hydrogenated to yield the desired 2-ethylhexanol. Although the preferred catalysts for such aldehyde hydrogenation reactions used to be Group VIII metal catalysts, such as nickel, palladium or platinum, the use of a solid catalyst comprising a reduced mixture of CuO and ZnO under vapour phase conditions has also been proposed (see EP-A-0008767 and U.S. Pat. No. 2,549,416). Molybdenum sulphide supported on an activated carbon carrier has also been suggested in GB-A-765972. The hydrogenation of an aldehyde feed containing ring-type sulphur compounds using a reduced mixture of oxides or hydroxides of copper and zinc is described in U.S. Pat. No. 4,052,467. Copper chromite has also been used as an aldehyde hydrogenation catalyst.

Hydrodesulphurisation is another commercially important hydrogenation reaction. This is the removal complex organic sulphur compounds, such as sulphides, disulphides, benzothiophene and the like, from a mixed hydrocarbon feedstock by catalytic reaction with hydrogen to form hydrogen sulphide. In such a process typical operating conditions include use of a temperature of from about 260° C. to about 375° C., a hydrogen pressure of from about 5 bar to about 40 bar and an alumina supported cobalt-molybdenum or nickel-molybdenum catalyst.

Catalytic hydrogenation is in all the above cases a heterogeneous process. It may be operated as a liquid phase process or as a vapour phase process. A review of some of the factors involved in designing heterogeneous gas and vapour phase reaction systems appeared in "Chemical Engineering", July 1955, in an article entitled "Moving Bed —Processes ... New Applications", at pages 198 to 206 (see in particular pages 204 and 205 thereof).

There have been various prior proposals to operate hydrogenation processes in several catalytic stages connected in series. For example, a vapour phase aldehyde hydrogenation process is described in U.S. Pat. No. 4,451,677 which involves use of a plurality of adiabatically operated catalytic hydrogenation stages connected in series.

DE-B-1115232 describes a process for the production of alcohols with 2 to 6 carbon atoms by hydrogenation in the liquid phase over a nickel or cobalt catalyst of a feed mixture comprising the corresponding aldehyde diluted with from 50 to 300 volume % of product alcohol, using two hydrogenation stages connected in series. Reaction conditions include use of a temperature of 130° C. to 220° C. and a pressure of less than 50 bar, whilst the aldehyde feed rate corresponds to a space velocity of from 0.3 to 2.5 $hr^{-1}$, preferably 0.75 to 1.1 $hr^{-1}$. An excess of hydrogen is recirculated from the exit end of the second hydrogenation stage to the inlet end of the first hydrogenation stage.

GB-A-784359 is concerned with preferential hydrogenation of aldehydes in a mixture of aldehydes and olefins, water being added to inhibit olefin hydrogenation. Multi-bed co-current hydrogenation is used, with injection of hydrogen between beds. Hydrogen recycle is envisaged.

GB-A-1175709 describes an apparatus for production of cyclohexane by catalytic hydrogenation of benzene. Excess hydrogen is recycled.

Use of 2-ethylhexanol as solvent to control the temperature during hydrogenation of a mixture of 2-ethylhexanal and iso-butyraldehyde is suggested in BR-A-PI800154 (Chem. Abs., 96 (1982) 51807h).

CA-A-926847 discloses in Example 2 a process in which a solution of 2-ethylanthraquinone is passed through a tubular reactor in co-current with hydrogen. U.S. Pat. No. 3,009,782 describes a similar process in which the working solution is passed through a fixed bed of the hydrogenation catalyst at a rate of between 20 and 200 liters per minute per square foot of catalyst bed cross-section (215.3 and 2152.8 liters per minute per square meter of catalyst bed). A further modification of this process is outlined in U.S. Pat. No. 3,755,552 which recommends hydrogenation in a hydrogenator shell containing a plurality of substantially vertically oriented, laterally positioned cylinders filled with catalyst wherein the ratio of the diameter of a cylinder to the diameter of the catalyst particle is at least 15:1.

In conventional liquid phase multi-stage hydrogenation processes the hydrogen-containing gas and the material to be hydrogenated are fed through the plant in co-current or in counter-current fashion. In order to achieve good economy of hydrogen usage it is usual to recycle gas within the plant. Hence in designing the plant account must be taken of the circulating inert gases (e.g. $N_2$, Ar, $CH_4$ and the like) which are inevitably present in the circulating gas of a commercial plant. Moreover, it is recognised in the art that hydrogen is relatively poorly soluble in organic liquids and so one of the rate limiting steps in a liquid phase hydrogenation process may be the dissolution of hydrogen in the organic phase and its subsequent migration through the liquid phase to the catalyst surface. For this reason the use of high partial pressures of hydrogen is often recommended, although often a balance has to be struck by the plant designer between additional process efficiency and the additional capital and running costs associated with use of high pressures. An extra factor to be considered is the additional cost of using recirculating gas streams at high pressure which contain significant levels of inert gases as well as hydrogen. Hence the plant designer may have to sacrifice efficiency of hydrogen utilisation in order to avoid the waste of energy involved in recycling inert gases at high pressures in excess of about 50 bar.

The term trickle bed reactor is often used to describe a reactor in which a liquid phase and a gas phase flow concurrently downward through a fixed bed of catalyst particles while reaction takes place. At sufficiently low liquid and gas flow rates the liquid trickles over the packing in essentially a laminar film or in rivulets, and the gas flows continuously through the voids in the bed. This is sometimes termed the gas continuous region or homogeneous flow and is the type encountered usually in laboratory and pilot scale operations. As gas and/or liquid flow rates are increased there is encountered behaviour described as rippling, slugging or pulsing flow. Such behaviour may be characteristic of the higher operating rates encountered in commercial petroleum processing. At high liquid rates and sufficiently low gas rates, the liquid phase becomes continuous and the gas passes in the form of bubbles; this is sometimes termed dispersed bubble flow and is characteristic of some chemical processing in which liquid flow rates are comparable to the highest encountered in petroleum processing, but where gas/liquid ratios are much less. Flow patterns and the transitions from one form to another as a function of gas and liquid flow rates have been described by several authors.

A useful general review of trickle bed reactors and other multiphase reactors can be found under the heading "Reactor Technology" in "Kirk-Othmer Encyclopedia of Chemical Technology", Third Edition, Volume 19, at pages 880 to 914. This states at page 892:

"Trickle-bed reactors have complicated and as yet poorly defined fluid dynamic characteristics. Contacting between the catalyst and the dispersed liquid film and the film's resistance to gas transport into the catalyst, particularly with vapor generation within the catalyst, is not a simple function of liquid and gas velocities Maximum contacting efficiency is attainable with high liquid mass velocities, i.e. 1–5 kg/(m²·s) or higher in all sized units however, 3–8 kg/(m²·s) is a more preferable range of liquid mass velocities."

Assuming a specific gravity for an organic liquid of approximately 0.8, these liquid velocities indicate that maximum contacting efficiency is attainable at a superficial liquid velocity of 0.24 to 1.0 cm/sec (i.e. 3–8 kg/(m²·s)).

Further reviews of the operation of trickle bed reactors have appeared as follows:
1. "Trickle-bed reactors" by Charles N. Satterfield, AIChE Journal, Vol. 21, No. 2 (March 1975), pages 209 to 228;
2. "Chemical Reactor Design for Process Plants" by H. F. Rase (1977), pages 698 to 711;
3. "Multiphase Catalytic Packed-Bed Reactors" by Hanns P. Hofmann, Catal Rev.-Sci. Eng., 17(1), pages 71 to 117 (1978);
4. "Encyclopedia of Fluid Mechanics" (1986), Chapter 32 by Milorad P. Dudukovic and Patrick L. Mills, pages 969 to 1017, published by Gulf Publishing Company, P. O. Box 2608, Houston, Tex. 77001;
5. "Trickle-Bed Reactors", by Mordechay Herskowitz and J. M. Smith, AIChE Journal, Vol. 29, No. 1 (January 1983) pages 1 to 18;
6. "Hydroprocessing conditions affect catalyst shape selection" by B. H. Cooper, B. B. L. Donnis, and B. Moyse, Technology, Dec. 8, 1986, Oil & Gas Journal, pages 39 to 44;
7. "Gas-Liquid-Solid Reaction Engineering" by Y. T. Shah and D. Smith, IChemE Symposium Series 87 (ISCRE 8);
8. "Trickle-Bed Reactors: Dynamic Tracer Tests, Reaction Studies, and Modeling of Reactor Performance" by A. A. El-Hisnawi, M. P. Dudukovic and P. L. Mills, ACS Symposium Series 196, Chemical Reaction Engineering (1982), pages 421 to 440;
9. "Hydrodynamics and interfacial areas in downward cocurrent gas-liquid flow through fixed beds. Influence of the nature of the liquid" by B. I. Morsi, N. Midoux, A. Laurent, and J.-C. Charpentier, International Chemical Engineering, Vol. 22, No. 1, pages 142 to 151 (January 1982);
10. "Packing wetting in trickle bed reactors: influence of the gas flow rate" by S. Sicardi, G. Baldi, V. Specchia, I. Mazzarino, and A. Gianetto, Chemical Engineering Science, Vol. 36, pages 226 to 227 (1981);
11. "Influence of gas velocity and packing geometry on pulsing inception in trickle-bed reactors" by S. Sicardi and H. Hofmann, The Chemical Engineering Journal, 20 (1980), pages 251 to 253;
12. "Some comments on models for evaluation of catalyst effectiveness factors in trickle-bed reactors" by P. L. Mills, H. F. Erk, J. Evans, and M. P. Dudukovic, Chemical Engineering Science, (1981), Vol. 36 (5), pages 947 to 950;
13. "Effectiveness Factors and Mass Transfer in Trickle-Bed Reactors" by Mordechay Herskowitz, R. G. Carbonell and J. M. Smith, AIChE Journal Vol. 25, No. 2 (March 1979) pages 272 to 283;
14. "Flow Regime Transition in Trickle-Bed Reactors" by S. Sicardi, H. Gerhard and H. Hoffmann, The Chemical Engineering Journal, 18 (1979), pages 173 to 182;
15. "Catalyst Effectiveness Factor in Trickle-Bed Reactors" by M. P. Dudukovic and P. L. Mills, Chemical Reaction Engineering—Houston, ACS Symposium Series 65 (1978), pages 387 to 399;
16. "Hydrodynamics and Solid-Liquid Contacting Effectiveness in Trickle-Bed Reactors" by A. Gianetto, G. Baldi, V. Specchia, and S. Sicardi, AIChE Journal, Vol. 24, No. 6, (November 1978), pages 1087 to 1104;
17. "Analysis of Three-Phase Packed-Bed Reactors" by S. Goto and J. M. Smith, AIChE Journal, Vol. 24, No. 2, pages 295 to 302;
18. "Performance of Slurry and Trickle-Bed Reactors Application to Sulfur Dioxide Removal", by S. Goto and J. M. Smith, AIChE Journal, Vol. 24, No. 2, March 1978 pages 286 to 293;
19. "Two-Phase Downflow Through Catalyst Beds: Part 1. Flow Maps" by E. Talmor, AIChE Journal, Vol. 23, No. 6, November 1977, pages 868 to 878;
20. "Pressure Drop and Liquid Holdup for Two Phase Concurrent Flow in Packed Beds" by V. Specchia and G. Baldi, Chemical Engineering Science, Vol. 32, (1977) pages 515 to 523;
21. "Trickle-Bed Reactor Performance: Part 1. Holdup and Mass Transfer Effects" by S. Goto and J. M. Smith, AIChE Journal, Vol. 21, No. 4, July 1975, pages 706 to 713;
22. "Effect of Holdup Incomplete Catalyst Wetting and Backmixing during Hydroprocessing in Trickle Bed Reactors" by J. A. Paraskos, J. A. Frayer and Y. T. Shah, Ind. Eng. Chem., Process Des. Dev., Vol. 14, No. 3, (1975) pages 315 to 322;
23. "Wetting of Catalyst Particles under Trickle Flow Conditions" by J-B Wijffels, J. Verloop and F. J. Zuiderweg, Chemical Reaction Engineering-II, Advances in Chemistry Series, Vol. 133, 1974, pages 151 to 163;
24. "The Role of Liquid Holdup and Effective Wetting in the Performance of Trickle-Bed Reactors" by D. E. Mears, Chemical Reaction Engineering-II, Advances in Chemistry Series, Vol. 133, 1974 pages 218 to 227;
25. "Scale Up of Pilot Plant Data for Catalytic Hydroprocessing" by H. C. Henry and J. B. Gilbert, Ind. Eng, Chem. Process Des. Develop., Vol. 12, No. 3, 1973, pages 328 to 334;
26. "Direct Solid-Catalyzed Reaction of a Vapor in an Apparently Completely Wetted Trickle Bed Reactor" by C. N. Satterfield and F. Ozel, AIChE Journal, Vol. 19, No. 6, November 1973, pages 1259 to 1261;
27. "Pressure Loss and Liquid Holdup in Packed Bed Reactor with Cocurrent Gas-Liquid Down Flow" by Y. Sato, T. Hirose, F. Takahashi, and M. Toda, Journal of Chemical Engineering of Japan, Vol. 6, No. 2, 1973, pages 147 to 152;
28. "Partial Wetting in trickle bed reactors—the reduction of crotonaldehyde over a palladium catalyst", by W. Sedriks and C. N. Kenney, Chemical Engineering Science, Vol. 28, 1973, pages 559 to 568;
29. "Handling kinetics from trickle-phase reactors" by A. Bondi, Chem. Tech., March 1971, pages 185 to 188;
30. "Kinetics of Hydrodesulfurization" by C. G. Frye and J. F. Mosby, Chemical Engineering Progress, Vol. 63, No. 9, September 1967, pages 66 to 70; and
31. "Performance of Trickle Bed Reactors" by L. D. Ross, Chemical Engineering Progress, Vol. 61, No. 10, October 1965, pages 77 to 82.

The present invention seeks to provide an improved liquid phase hydrogenation process in which essentially 100% hydrogenation of the aldehyde or other organic feedstock to the desired hydrogenation product can be achieved, with minimisation of formation of by-products.

It further seeks to provide a liquid phase hydrogenation process in which the use of gas recycle compressors is obviated. Additionally it seeks to provide a process for liquid phase hydrogenation of a wide variety of organic feedstocks which can be operated with excellent economy of hydrogen usage without the need for recycle of hydrogen-containing gases.

According to the present invention there is provided a liquid phase catalytic hydrogenation process in which an organic feedstock is contacted with hydrogen in the presence of a solid hydrogenation catalyst under hydrogenation conditions to produce a hydrogenation product, which process comprises passing a feed solution of the organic feedstock in an inert diluent therefor downwardly in co-current with a hydrogen-containing gas through a hydrogenation zone containing a bed of a particulate hydrogenation catalyst whose particles substantially all lie in the range of from about 0.5 mm to about 5 mm, maintaining the bed of catalyst particles under temperature and pressure conditions conducive to hydrogenation, recovering from a bottom part of the bed a liquid phase containing the hydrogenation product, controlling the rate of supply of the feed solution to the bed so as to maintain a superficial liquid velocity of the liquid down the bed in the range of from about 1.5 cm/sec to about 5 cm/sec, and controlling the rate of supply of the hydrogen-containing gas to the bed so as to maintain at the top surface of the bed of catalyst particles a flow of hydrogen-containing gas containing from 1.00 to about 1.15 times the stoichiometric quantity of hydrogen theoretically necessary to convert the organic feedstock completely to the hydrogenation product.

Preferably the catalyst particle size range is from about 0.5 mm to about 3 mm.

In view of the teaching in the art that, in operation of trickle bed reactors, the maximum gas-liquid contacting efficiency is attainable at a superficial liquid velocity of no more than about 1.0 cm/sec, it is most surprising to find that, in hydrogenation reactions such as the hydrogenation of an aldehyde to an alcohol, an approximately stoichiometric quantity of hydrogen, or at most only a minor excess of hydrogen, can be used to achieve near quantitative hydrogenation in a single passage over a bed of catalyst of the appropriate depth when the catalyst particle size range is from about 0.5 mm to about 5 mm and a high liquid superficial velocity down the bed, i.e. from about 1.5 cm/sec to about 5 cm/sec, is used. Thus, even though the gas near the exit end of the bed may be almost entirely depleted of hydrogen, efficient conversion of unsaturated organic compound (e.g. aldehyde) or other organic feedstock to hydrogenatipn product (e.g. alcohol) can be achieved without having to have recourse to high pressures in excess of about 50 bar. Hence the use of a large excess of hydrogen is not necessary as we have shown, in the course of our experimentation, that the influence of hydrogen partial pressure on the rate of hydrogenation is of minor significance. Moreover in our work on hydrogenation of aldehydes we have found that, under the unconventional flow conditions used in the process of the invention, high average rates of reaction are possible, approaching in suitable cases about 5 gm. moles of aldehyde hydrogenated per liter of catalyst per hour and at the same time achieving substantial conversion (i.e. 95% of more) of the aldehyde feed to the alcohol product.

The process of the invention is not specific to any particular hydrogenation reaction or to any particular catalyst composition. However, in general the hydrogenation conditions used in the hydrogenation zone include use of a pressure of from about 1 bar to about 300 bar, often from about 1 bar to about 100 bar, and of a temperature of from about 40° C. to about 350° C., often from about 90° C. to about 220° C.

In operating the process of the invention a pressure drop is set up across the catalyst bed, typically of at least about 0.1 kg/cm$^2$ per meter of catalyst bed depth. Care must accordingly be taken, in designing a plant to operate according to the invention, that it is ensured that at the bottom of the catalyst bed the crushing strength of the catalyst is not equalled or exceeded. If there is any risk of this occurring, then it is necessary to utilise two or more catalyst beds of appropriate depth in place of a single large catalyst bed; in this case gas and liquid must be uniformly distributed into each bed.

The selection of catalyst particle size and of the superficial liquid velocity are features which are crucial to the process of the invention. These features ensure that the catalyst surface is completely wetted, that a large catalyst superficial surface area is presented for reaction of the unsaturated organic compound or other organic feedstock with hydrogen, that good liquid-gas contact is effected as the gas bubbles entrained in the liquid pass through the irregular channels in the bed in co-current downflow through the bed, that dissolution of hydrogen into the downflowing liquid is thereby facilitated, and that good mass transfer of the dissolved hydrogen and unsaturated organic compound or other organic feedstock to the catalyst surface is also achieved by the relatively rapid flow of the liquid through the complex network of interconnecting passages present in the catalyst bed. In the case of spherical catalyst particles the actual velocity of the liquid over the catalyst surface can be up to about 3 times the superficial velocity of the gas plus liquid. Another important factor is the concentration of the unsaturated organic compound or other organic feedstock in the liquid phase. As hydrogenation is usually an exothermic reaction, the use of an appropriately dilute solution helps to limit the temperature rise, particularly when the hydrogenation zone is operated under adiabatic conditions. By selection of an appropriate concentration of unsaturated organic compound or other organic feedstock in the feed solution it is possible to optimise hydrogenation conditions at the catalyst surface so that neither the unsaturated organic compound or other organic feedstock nor any hydrogenation product thereof "blinds" the catalyst to hydrogen. Such "blinding" of the catalyst will occur, it is postulated, if one or more of the species present, whether the unsaturated organic compound or other organic feedstock or some hydrogenation product thereof, is strongly absorbed or adsorbed on the catalyst surface and thereby prevents approach of hydrogen molecules to the active catalytic sites.

The process of the invention can be applied, for example to the hydrogenation of unsaturated hydrocarbons to saturated hydrocarbons. Typical of such a reaction is the production of cyclohexane from benzene. This hydrogenation can be carried out according to the invention using a nickel, palladium or platinum catalyst in the hydrogenation zone and a temperature of from about 100° C. to about 200° C. and a pressure of from about 5 bar to about 30 bar. This reaction is exothermic. The use of relatively high temperatures is normally recommended so as to maximise the rate of conversion of benzene to cyclohexane, but isomerisation of cyclohexane to methyl cyclopentane, which is extremely difficult to separate from cyclohexane, can occur in the aforementioned conventional procedures, especially at such relatively high temperatures.

Production of secondary alcohols by reduction of ketones is another appropriate hydrogenation reaction to which the invention can be applied Examples of such reactions include production of iso-propanol from acetone and of cyclohexanol from cyclohexanone.

Another example of a hydrogenation reaction to which the present invention can be applied is the production of butane-1,4-diol by hydrogenation of but-2-yn-1,4-diol This can be carried out using a catalyst which is a granular nickel-copper-manganese on silica gel at a pressure of from about 200 bar to about 300 bar in the hydrogenation zone. A typical inlet temperature to the hydrogenation zone is about 40° C., when the catalyst is freshly reduced A further example of a hydrogenation reaction to which the process of the invention can be applied is the production of stearic acid by hydrogenation of linoleic acid, of linolenic acid, or of a mixture thereof This can be carried out using a nickel, cobalt, platinum, palladium, chromium or zinc catalyst at a pressure of from about 10 bar to about 40 bar and an inlet temperature to the hydrogenation zone of about 150° C.

Other examples of hydrogenation processes to which the invention can be applied include "hardening" of vegetable oils, hydrodesulphurization, hydrogenation of nitriles to amines, and hydrogenation of sugars, (for example, hydrogenation of aldoses, such as D-glucose or D-mannose, to the corresponding hexahydroxyalcohols, such as sorbitol and mannitol).

A particularly preferred type of hydrogenation reaction is the production of alcohols from aldehydes. Such aldehydes generally contain from 2 to about 20 carbon atoms and may in the case of those aldehydes containing 3 or more carbon atoms include one or more unsaturated carbon-carbon bonds besides the unsaturated —CHO group. Thus as used herein the term "aldehyde" includes both saturated and unsaturated aldehydes, that is to say aldehydes wherein the only hydrogenatable group is the aldehyde group, —CHO, itself (such as alkanals) and aldehydes which contain further hydrogenatable groups such as olefinic groups, $>$C=C$<$, in addition to the aldehyde group, —CHO (such as alkenals). Typical aldehydes include n- and iso-butyraldehydes, n-pentanal, 2-methylbutanal, 2-ethylhex-2-enal, 2-ethylhexanal, 4-t-butoxybutyraldehyde, $C_{10}$—"OXO"—aldehydes (e.g. 2-propylhept-2-enal), undecanal, dodecanal, tridecanal, crotonaldehyde and furfural, as well as mixtures of two or more thereof. Aldehydes and mixtures of aldehydes can be produced by hydroformylation of an olefin or mixed olefins in the presence of a cobalt catalyst or a rhodium complex catalyst, according to the equation: R·CH=CH$_2$+H$_2$+CO→R·CH$_2$·CH$_2$·CHO+R·CH(-CHO)·CH$_3$; where R is a hydrogen atom or an alkyl radical. The ratio of the n-aldehyde to the iso-aldehyde in the product depends to a certain extent on the selected hydroformylation conditions and upon the nature of the hydroformylation catalyst used. Although cobalt catalysts were formerly used, more recently the use of rhodium complex catalysts has been preferred since these offer the advantages of lower operating pressure, ease of product recovery, and high n-iso-aldehyde molar ratios. Typical operating conditions for such rhodium complex hydroformylation catalysts can be found in U.S. Pat. No. 3,527,809, U.S. Pat. No. 4,148,830, EP-A-0096986, EP-A-0096987, and EP-A-0096988. In such hydroformylation processes the aldehyde or aldehyde products can be recovered in admixture with unreacted olefin and its hydrogenation product, i.e. the corresponding paraffin. Such crude reaction products can be used as starting material in the process of the invention. Further aldehydes can be obtained by condensation reactions; for example, 2-ethylhex-2-enal can be made by condensation of 2 moles of n-butyraldehyde and 2-propylhept-2-enal by condensation of 2 moles of n-valeraldehyde. Examples of aldehyde hydrogenation reactions are the production of n-butanol from n-butyraldehyde, of 2-ethylhexanol from 2-ethylhex-2-enal, or 2-propylheptanol from 2-propylhept-2-enal, of undecanol from undecanal, and of 4-t-butoxybutanol from 4-t-butoxybutyraldehyde. The invention is used to special advantage for hydrogenation of aldehydes containing from about 7 to about 17 carbon atoms to the corresponding alkanols. In such aldehyde hydrogenation reactions there can be used any of the conventionally used supported metal catalysts, such as Ni, Pd or Pt supported on a variety of supports such as granular carbon, silica, silica-alumina, zirconia, silicon carbide or the like, or copper chromite.

Other aldehyde hydrogenation catalysts include cobalt compounds; nickel compounds which may contain small amounts of chromium or another promoter; mixtures of copper and nickel and/or chromium; and other Group VIII metal catalysts, such as Pt, Pd, Rh and mixtures thereof, on supports, such as carbon, silica, alumina and silica-alumina. The nickel compounds are generally deposited on support materials such as alumina or kieselguhr.

In all cases the catalyst particles substantially all have a particle size in the range of from about 0.5 mm to about 5 mm, preferably in the range of from about 0.5 mm to about 3 mm, as measured by a conventional sieve analysis techhique. By the term "substantially all" we mean that not more than about 5%, and preferably not more than about 0.5%, of particles are less than about 0.5 mm in size, and that not more than about 5%, and preferably not more than about 1%, of particles are larger than 5 mm (or 3 mm) in size. The catalyst particles may be of any desired shape, such as cylindrical, but are conveniently approximately spherical granules. However the use of pelleted catalysts and of catalyst particles of more complex shape is not ruled out. In the case of spherical or granular catalyst particles the particle size is essentially equivalent to particle diameter, whereas in the case of cylindrical catalyst particles or particles of more complex shape the size range refers to the shortest particle dimension, e.g. diameter in the case of a cylinder or extrudate. Particularly preferred catalysts are those with a particle size range of from about 1 mm to about 2 mm.

The hydrogenation zone may include two or more beds of catalyst. Conveniently, however, the hydrogenation zone comprises a single catalyst bed. The depth of the catalyst bed or beds should be sufficient to ensure that the desired degree of conversion (e.g. about 75% to about 99% or higher, for example about 99.5% or more) can be effected in passage through the bed under the selected reaction conditions.

The hydrogen-containing gas supplied to the hydrogenation zone preferably contains a major amount of hydrogen and at most a minor amount of one or more inert gases, such as nitrogen, methane, other low molecular weight hydrocarbons, such as ethane, propane, n-butane and iso-butane, carbon oxides, neoh, argon or the like. Preferred hydrogen-containing gases are accordingly gases containing at least about 50 mole % up to about 95 mole % or more (e.g. about 99 mole %), of $H_2$ with the balance comprising one or more of $N_2$, CO, $CO_2$, Ar, Ne, $CH_4$ and other low molecular weight saturated hydrocarbons. In some cases, for example when using nickel catalysts, the presence of CO and $CO_2$ cannot be tolerated and the total carbon oxides concentration should not, in this case, be more than about 5 to 10 ppm by volume. Such hydrogen-containing gases can be obtained in conventional manner from synthesis gas and other usual sources of hydrogen-containing gases, followed, if necessary, by appropriate pretreatment to remove impurities, such as sulphurous impurities (e.g. $H_2S$, COS, $CH_3SH$, $CH_3SCH_3$, and $CH_3SSCH_3$) and halogen-containing impurities (e.g. HCl and $CH_3Cl$) which would exert a deleterious influence on catalytic activity, i.e. catalyst inhibition, poisoning or deactivation, as well as by the removal of the carbon oxides. Preparation of suitable hydrogen-containing gases will accordingly be effected according to usual production techniques and forms no part of the present invention. Thus the hydrogen-containing gas supplied to the hydrogenation zone may be, for example, a 94 mole % hydrogen stream produced by steam reforming of natural gas followed by the water gas shift reaction:

$$CO + H_2O \rightleftharpoons CO_2 + H_2,$$

then by $CO_2$ removal to give a gas containing about 1 mole % to about 2 mole % carbon oxides, and finally by methanation to give a gas containing only a few ppm by volume of carbon oxides. Substantially pure hydrogen from an electrolysis plant may be used, as can also purified hydrogen streams obtained by the pressure swing adsorption treatment of hydrogen admixed with CO, $CO_2$ and light hydrocarbon gases, in each case with excellent results. For a discussion of production of hydrogen streams by pressure swing adsorption reference may be made to a paper entitled "Hydrogen Purification by Pressure Swing Adsorption" by H. A. Stewart and J. L. Heck, prepared for Symposium on Adsorption—Part III, 64th National Meeting of the American Institute of Chemical Engineers, New Orleans, La., U.S.A., March 16-20, 1969.

The rate of supply of the feed solution to the catalyst bed corresponds to a superficial liquid velocity down the bed of from about 1.5 cm/sec to about 5 cm/sec, for example from about 1.5 cm/sec to about 3 cm/sec.

The feed solution supplied to the hydrogenation zone contains the unsaturated organic compound or other organic feedstock dissolved in a compatible diluent therefor. The purpose of the diluent is to act as a heat sink, to limit the temperature rise within the hydrogenation zone to an acceptable limit, and also to provide at the same time an appropriate volumetric flow into the catalyst bed, such that the required liquid superficial velocity is achieved along with the desired product conversion and temperature rise. The concentration of organic feedstock in the feed solution is accordingly preferably selected in dependence on the expected acceptable temperature rise across the hydrogenation zone; such temperature rise should not be so great as to cause more than a minor amount of vaporisation of liquid in the hydrogenation zone or to cause thermal damage to the catalyst, to any reactant present or to the hydrogenation product.

In a typical process the feed solution supplied to the hydrogenation zone contains at least about 1 mole % of an unsaturated organic compound up to about 50 mole %, more preferably in the range of from about 5 mole % up to about 33 mole %, the balance being diluent or diluents.

In a typical hydrodesulphurisation process the organic feedstock comprises one or more organic sulphurous compounds present in a hydrocarbon diluent. The concentration of such sulphurous compounds (expressed as sulphur content) may range from a few ppm, e.g. about 5 ppm up to about 10% by weight.

The diluent can be any convenient inert liquid or mixture of liquids that is compatible with the unsaturated organic compound or other organic feedstock and the catalyst, with any intermediate product or by-product, and with the desired hydrogenation product. In many cases the hydrogenation product itself can be used as the compatible diluent or as a part of the compatible diluent. Hence, when hydrogenating an aldehyde for example, the diluent can be the product alcohol obtained upon hydrogenation of the aldehyde. In this case the process of the invention includes the further step of recycling a part of the liquid hydrogenation product for admixture with make up unsaturated organic compound or other organic feedstock to form the feed solution to the hydrogenation zone. Alternatively aldehyde condensation product, such as the dimers, trimers and high condensation products of the type disclosed in GB-A-1338237, can be used as diluent. If the unsaturated organic compound or other organic feedstock used as starting material is a solid or if the hydrogenation product or an intermediate product is a solid, then an inert solvent will usually be used. Similarly, use of a solvent may be desirable in cases in which by-product formation is a problem. For example, hydrazobenzene is a potential by-product of the hydrogenation of nitrobenzene to yield aniline; in such a case it is desirable to dissolve the unsaturated organic compound, such as nitrobenzene, in a solvent, such as ethanol, in order to limit formation of an undesirable by-product, such as hydrazobenzene. In this case it is also highly advantageous to include a minor amount of ammonia in the ethanol solvent as ammonia further limits the formation of by-products such as azobenzene, azoxybenzene or hydroazobenzene.

Because a stoichiometric or near stoichiometric quantity of hydrogen is used in the process of the invention and there is at most only a small excess of hydrogen used, the liquid phase hydrogenation of even relatively volatile unsaturated organic compounds to similarly volatile products, such as n-butyraldehyde to n-butanol, or benzene to cyclohexane, can be effected with essentially no risk of any part of the catalyst bed becoming dry. The use of a recycled inert liquid diluent to prevent an overall adiabatic temperature rise over the catalyst bed of not more than, typically, about 20° C. to 30° C. in combination with "forced irrigation" of all parts of the catalyst bed by the use of the unconventionally high superficial liquid velocity through the catalyst bed prevents the formation of "dry pockets" in the catalyst bed. The formation of such "dry pockets" where organic vapours and hydrogen are in contact with dry catalyst, in the absence of a continuous liquid flow to remove the heat, can lead to highly exothermic side reactions, e.g. hydrogenolysis of alcohols to hydrocarbons and water, leading to local temperature runaways, causing poor efficiency of hydrogenation to the desired product, and reduced catalyst life, as well as reduced catalyst utilization efficiency, and even to the formation of tarry materials, or in some cases, to solid coke-like substances.

The hydrogenation zone may comprise an adiabatic reactor, a reactor with an internal cooling coil, or a shell and tube reactor. In the case of a shell and tube reactor the catalyst may be packed in the tubes with coolant passing through the shell or it may be the shell that is packed with catalyst with coolant flow through the tubes. The choice of reactor design will usually be influenced by such factors as the exothermicity of the reaction at the selected inlet concentration of unsaturated organic compound or other organic feedstock, the thermal sensitivity of the catalyst, and the temperature dependence of any by-product formation reaction, as well as by fluid flow considerations to ensure that even distribution of gas and liquid within the catalyst volume is obtained. Generally, however, when an adiabatic temperature rise across the catalyst bed of from about 20° C. to about 30° C. can be accepted, a simple hydrogenation reactor consisting of one or more beds of catalyst in a cylindrical vessel with its axis arranged vertically can be used with good results. When two or more beds are used in such a reactor the space between adjacent beds will be largely occupied by the gas phase. The liquid emerging from one bed may with advantage be collected and passed over a distributor of conventional design before entering the next bed.

The hydrogen containing gas is generally admixed with the feed solution upstream from the hydrogenation zone and is partly dissolved therein. At the upper end of the hydrogenation zone the concentration of unsaturated organic compound or other organic feedstock is at its highest in the liquid phase; hence the rate of hydrogenation is greatest at the upper end of the hydrogenation zone. As the liquid phase passes downwardly through the bed of catalyst particles co-currently with the hydrogen it becomes depleted in respect of hydrogenatable material and to some extent in respect of dissolved hydrogen. The dissolved hydrogen is continuously replenished from the gas phase at a rate which is dependent upon the difference between the actual concentration of dissolved hydrogen and the concentration of dissolved hydrogen at saturation in the liquid. As a result of the depletion of hydrogen from the gas phase the partial pressure of any inert gas or gases present rises and the partial pressure of hydrogen falls as the hydrogen is consumed by the chemical reactions taking place in the hydrogenation zone. Hence at the lower end of the hydrogenation zone the driving force for the hydrogenation reaction can be relatively low. The reaction product exiting the lower end of the hydrogenation zone accordingly usually still contains a minor amount of chemically unsaturated or other hydrogenatable material. Typically the reaction product exiting the hydrogenation zone contains from about 0.01 mole % to about 0.5 mole %, up to about 5 mole % or more of chemically unsaturated or other hydrogenatable organic material.

As already mentioned, the organic feedstock used as starting material may be an unsaturated organic compound that includes two or more hydrogenatable unsaturated groups which may undergo more or less selective hydrogenation in passage through the hydrogenation zone. For example, when an olefinically unsaturated aldehyde (such as 2-ethylhex-2-enal) is hydrogenated, the olefinic bond tends to be hydrogenated first, before the aldehyde group, so that the saturated aldehyde (such as 2-ethylhexanal) is a recognisable intermediate product. However, some hydrogenation of the aldehyde group may occur prior to hydrogenation of the olefinic linkage, so that 2-ethylhex-2-enol is an alternative intermediate product but is generally formed in lesser amounts. Each of these intermediates can then undergo hydrogenation to the desired alcohol product, e.g. 2-ethylhexanol.

When an unsaturated organic compound is used as starting material that contains only a single hydrogenatable linkage then the unsaturated hydrogenatable organic material in the reaction product exiting the hydrogenation zone will comprise the unsaturated organic compound itself. However, when an unsaturated organic compound is used as starting material that contains more than one hydrogenatable unsaturated linkage, then the unsaturated hydrogenatable organic material in the reaction product exiting the hydrogenation zone will be selected from the starting material and any partially hydrogenated intermediates. For example, when hydrogenating 2-ethylhex-2-enal, the hydrogenatable unsaturated organic material in the reaction product may be selected from 2-ethylhex-2-enal, 2-ethylhexanal, 2-ethylhex-2-enol, and a mixture of two or more thereof.

Generally speaking the depth of the catalyst bed and the hydrogenation conditions in the hydrogenation zone are selected so as to effect hydrogenation of from about 75% to about 99% or more of any hydrogenatable groups present in the organic feedstock supplied to the hydrogenation zone. Typically the hydrogenation is completed to an extent of from about 85% to about 99.5% in the hydrogenation zone. In zone cases, however, the extent of hydrogenation in passage through the hydrogenation zone may be higher than this, e.g. 99.8% or more up to about 99.95%. Such hydrogenation conditions include supply of hydrogen-containing gas to the upper part of the hydrogenation zone in an amount sufficient to supply an amount of hydrogen that is greater than or equal to the stoichiometric quantity required to effect the desired degree of hydrogenation in the hydrogenation zone. Usually it will be desirable to limit the supply of hydrogen-containing gas thereto so as to provide as nearly as possible such stoichiometric quantity of hydrogen and thereby to minimise hydrogen losses in the purge stream from the plant. The rate of supply of hydrogen-containing gas to the hydrogenation zone will be mainly dependent upon its composition. It will often be preferred to limit the rate of supply so as to provide not more than about 115% (e.g. up to about 110%), and even more preferably not more than about 105% (e.g. about 102%), of the stoichiometric quantity required to effect the desired degree of hydrogenation in the hydrogenation zone.

If the hydrogen containing gas is substantially pure hydrogen, e.g. if it contains about 99.5 mole % or more of hydrogen, then very high degrees of hydrogenation, exceeding about 99% in suitable cases, can be achieved with the use of a low stoichiometric excess (e.g. about 102%) of hydrogen in a single hydrogenation zone. If, however, the available hydrogen containing gas is of moderate purity (e.g. one containing about 80 to about 90 mole % hydrogen) or of low purity (e.g. one containing less than about 80 mole % hydrogen), then the process can still be operated using only a low stoichiometric excess of hydrogen by use of two hydrogenation zones in series, as taught by WO-A -88/05767 published 11th August 1988 the disclosure of which is herein incorporated by reference. Any second or successive hydrogenation zone operating under a co-current flow regime is also desirably operated according to the teachings of the present invention.

The composition of the feed solution will depend upon factors such as the exothermicity of the hydrogenation reaction, the maximum permissible temperature rise in the hydrogenation zone, the design of the hydrogenation zone, and the maximum permissible rate of supply to the hydrogenation zone. When operating under adiabatic conditions with an unsaturated organic compound as the organic feedstock, the unsaturated organic compound (e.g. aldehyde):inert diluent molar ratio typically ranges from about 1:3 to about 1:10 and the rate of supply of feed solution to the hydrogenation zone ranges up to a rate corresponding to supply of unsaturated organic compound of about 8 moles per liter of catalyst per hour or more, e.g. up to about 10 or even 12 moles of aldehyde or other unsaturated organic compound per liter of catalyst per hour. If, however, provision is made for cooling the hydrogenation zone as, for example, by use of internal cooling coils within the catalyst bed or by use of a shell and tube reactor, then a higher concentration of unsaturated organic compound can be used; hence in this case the unsaturated organic compound:inert diluent molar ratio typically ranges from about 1:1 up to about 1:10.

The inlet temperature to the hydrogenation zone will be at least as high as the threshold temperature for the reaction and will be selected in dependence on the nature of the hydrogenation reaction. It will normally lie in the range of from about 40° C. to about 350° C., whilst the operating pressure typically lies in the range of from about 1 bar to about 300 bar. For example when hydrogenating an aldehyde by the process of the invention the inlet temperature to the hydrogenation zone is typically from about 90° C. to about 220° C. and the pressure is typically from about 5 to about 50 bar.

Besides any remaining hydrogenatable organic feedstock and the hydrogenation product and diluent (if different from the hydrogenation product), the liquid reaction product leaving the hydrogenation zone also contains dissolved inert gases and hydrogen. The gas phase leaving the hydrogenation zone contains a higher level of inert gases than the hydrogen-containing gas supplied to the upper part of the hydrogenation zone because hydrogen has been removed by the hydrogenation reaction in passage through the hydrogenation zone.

The reaction product exiting the hydrogenation zone (hereafter sometimes called "the first-mentioned hydrogenation zone") may be passed through a further hydrogenation zone in countercurrent to, or in co-current with, a flow of hydrogen-containing gas, in accordance with the teachings of WO-A-87/07598 published 17th December 1987 or of WO-A-88/05767 published 11th August 1988, the disclosure of each of which is herein incorporated by reference, for the purpose of removing final traces of hydrogenatable organic material. When any further hydrogenation zone is operated with co-current flow of hydrogen and liquid, it is preferred to operate such further hydrogenation zone also according to the teachings of the present invention.

When counter-current flow is used in the further hydrogenation zone, as taught by WO-A-87/07598 published 17th December 1987, the liquid phase from the bottom of the first-mentioned hydrogenation zone is fed in liquid form in countercurrent to an upward flow of hydrogen-containing gas. The gas fed to the further hydrogenation zone may have the same composition as that supplied to the first-mentioned hydrogenation zone. It is fed to the further hydrogenation zone generally in lesser amounts than the amount of hydrogen-containing gas supplied to the first-mentioned hydrogenation zone. Generally speaking, it should be fed to the further hydrogenation zone in an amount sufficient to provide an at least stoichiometric amount of hydrogen corresponding to the amount of hydrogenatable material remaining in the liquid phase recovered from the bottom of the first-mentioned hydrogenation zone. Usually it will be preferred to supply hydrogen-containing gas to the further hydrogenation zone at a rate sufficient to supply not more than about 115% (e.g. up to about 110%), preferably not more than about 105% (e.g. about 102%), of the stoichiometric quantity of hydrogen required to complete the hydrogenation of the hydrogenatable organic material in the liquid phase from the first-mentioned hydrogenation zone.

If desired, the gas fed to the further hydrogenation zone in countercurrent to the liquid flow may be richer in hydrogen than that fed to the first-mentioned hydrogenation zone. Hence the gas fed to the first-mentioned hydrogenation zone may be, for example, a 3:1 molar $H_2:N_2$ mixture obtained by conventional methods from synthesis gas, whilst the hydrogen stream to the further hydrogenation zone is a substantially pure $H_2$ stream formed by subjecting the same $H_2:N_2$ mixture to purification e.g. by pressure swing absorption.

In the further hydrogenation zone the highest $H_2$ partial pressure exists at the lower end thereof under a counter-current flow regime. Hence the driving f towards the desired hydrogenation product is maximised in the further hydrogenation zone and essentially all of the remaining unsaturated material in the liquid phase exiting the first-mentioned hydrogenation zone is hydrogenated in passage through the further hydrogenation zone.

An effluent stream comprising inert gases and hydrogen may be taken from the plant between the first-mentioned and further hydrogenation zones in this preferred process which utilises a counter-current flow regime in the further hydrogenation zone. This may be passed through a condenser in order to substantially recover any vaporised organic compounds therein. The resulting condensate is conveniently returned to the top of the further hydrogenation zone.

The catalyst beds of the first-mentioned and further hydrogenation zones will usually each be supported on a suitable grid. When both beds are mounted in the same vessel, liquid intermediate reaction product from the first-mentioned hydrogenation zone may simply be allowed to drop straight on top of the catalyst bed of the further hydrogenation zone when counter-current flow is used in the further hydrogenation zone. Usually, however, it will be desirable to collect and then to redistribute the liquid phase from the first-mentioned hydrogenation zone evenly over the upper surface of the catalyst bed of the further hydrogenation zone with the aid of a suitable liquid distribution device. In some cases it may be desirable to collect and redistribute liquid within the first-mentioned and/or further hydrogenation zones.

In a preferred process according to the invention for hydrogenation of an aldehyde the entry temperature to the first-mentioned hydrogenation zone lies in the range of from about 90° C. to about 220° C. and the pressure lies in the range of from about 5 bar to about 50 bar.

In operation of the process of the invention, under steady state conditions, the composition of the gas (whether dissolved in the liquid phase or present in the gaseous state) exhibits a significant variation between different parts of the plant. Thus, for example, the partial pressure of hydrogen is highest in the, or in each, hydrogenation zone at the respective gas inlet end thereof and lowest at the exit end for gaseous effluent therefrom, whilst the combined partial pressures of any inert materials present is lowest at the respective gas inlet end to the, or to each, hydrogenation zone and highest at the exit end for gaseous effluent therefrom. It is thus possible to discharge from the hydrogenation zone a purge gas containing about 50 mole % or more, typically at least about 75 mole %, of inert gases and less than about 50 mole % of hydrogen, typically less than about 25 mole % of hydrogen. Under suitable operating conditions it is possible to operate the process of the invention so that the effluent gases contain a relatively small concentration of hydrogen (e.g. 25 mole % or less) and consist predominantly of inert gases (e.g. $N_2$, Ar, $CH_4$ etc). In this case the effluent gas stream or streams from the plant is or are relatively small and consequently hydrogen losses are minimal. In general the composition and rate of withdrawal of the purge gas stream or streams will be dependent in large part upon the level of inert gases in the hydrogen containing gas. In the limit, when operating with very pure hydrogen, the solubility of inert gases in the reactor effluent is sufficient to purge such inert gases from the plant and it becomes unnecessary to purge an effluent gas stream from the hydrogenation zone, the inert gases being purged in the course of work up of the hydrogenation product.

Because any inert gases present are automatically concentrated in any gaseous effluent stream or streams, it is not necessary on economic grounds to recycle the gaseous effluents from the hydrogenation zone or zones so as to obtain efficient usage of hydrogen. Recycle of gas is necessary in conventional co-current or counter-current hydrogenation processes in order to achieve efficiency of operation. Moreover, as it is not necessary to recycle a gas stream which contains appreciable concentrations of inert gases so as to achieve satisfactory economy of hydrogen consumption, the total operating pressure of the plant can therefore be reduced although the hydrogen partial pressure is maintained; hence the construction costs can be reduced as the plant not only operates at a lower pressure but also no gas recycle compressor is needed. The absence of a gas recycle compressor, which is in itself an expensive item of equipment, means also that the civil engineering work associated with its installation, such as provision of a mounting and a compressor house therefor, is obviated. In addition the ancillary items of equipment normally needed when a gas recycle compressor is installed, such as a drive motor, power transformer, and instrumentation, are not required. There is also a saving in pipework for the plant as no provision for recycle of gas is needed. Although it is difficult to generalise, preliminary calculations suggest that the overall capital savings that can be achieved by adopting the process of the invention for an aldehyde hydrogenation plant with a throughput of 50,000 tonnes per year can be as much as about 20% compared with the cost of a conventionally designed aldehyde hydrogenation plant. Hence all of these factors have a significant effect on both capital and operating costs, both of which are lower for a plant constructed to operate the process of the invention than for conventional co-current or counter-current hydrogenation plants. Moreover, particularly in the case when a further hydrogenation zone is included in the plant as a "polishing" reactor for removal of the usually small amounts of hydrogenatable organic materials present in the liquid phase from the first-mentioned hydrogenation zone, which acts as a "bulk" hydrogenator for hydrogenation of the majority of the unsaturated organic compound, the downstream processing of the hydrogenation product is greatly facilitated as the product from the plant is essentially pure hydrogenation product. This also has a profound and beneficial effect on the capital cost and running costs of the product purification section.

Figure 5:
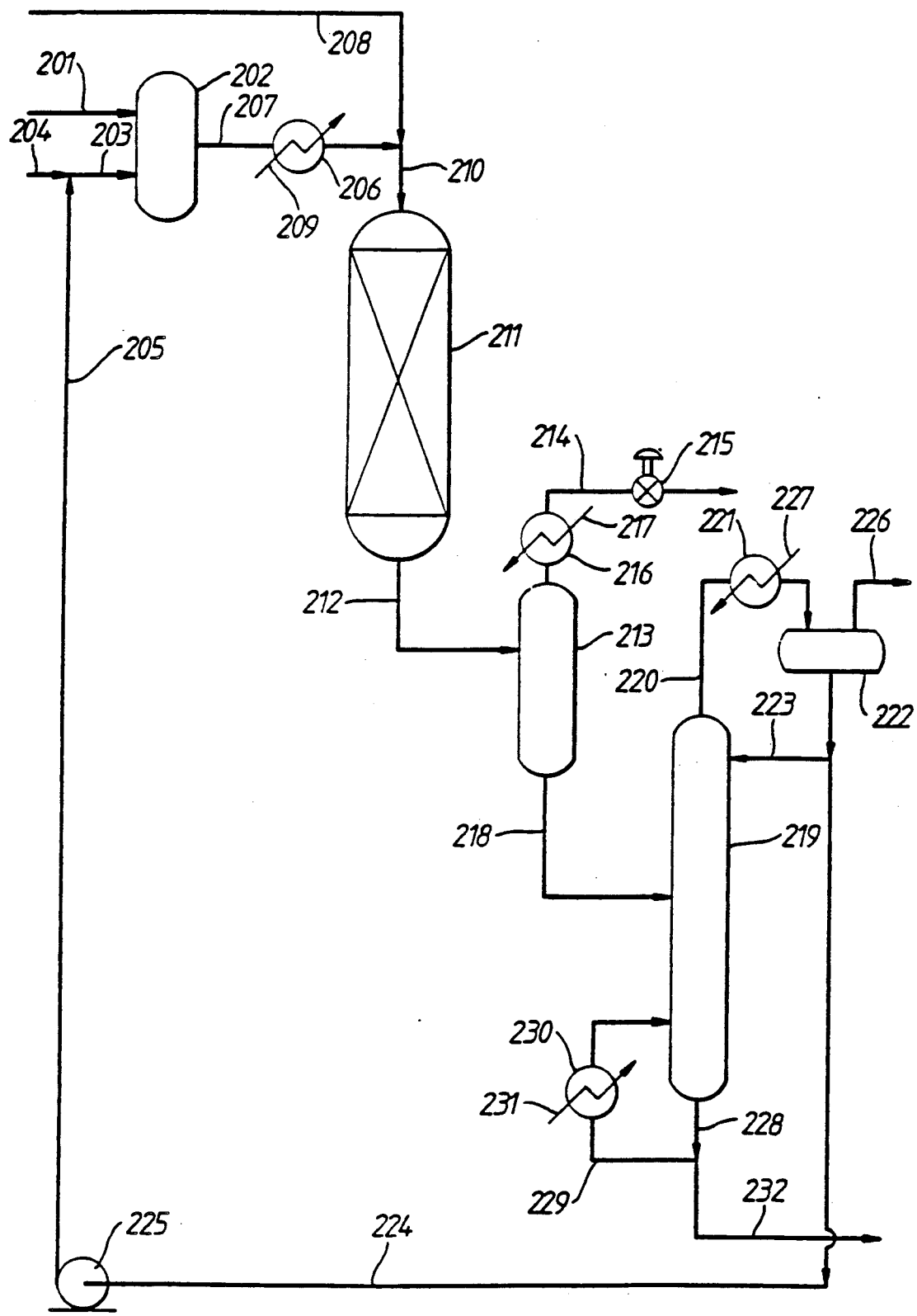
Figure 6:
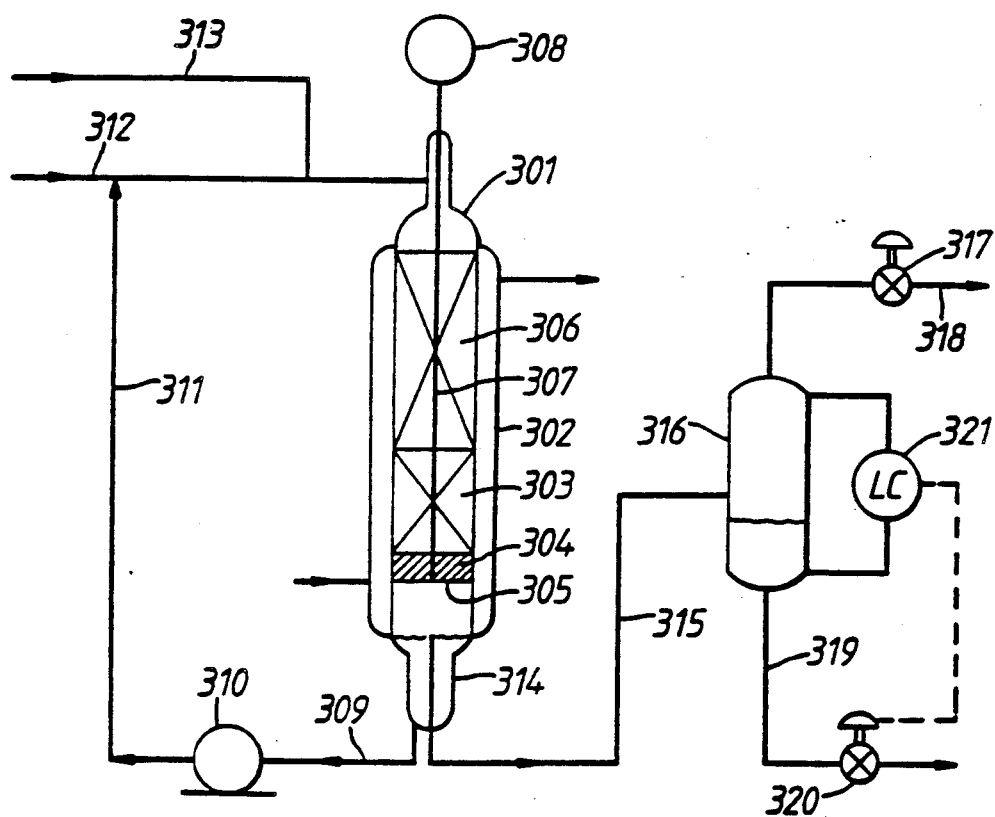
Figure 7:
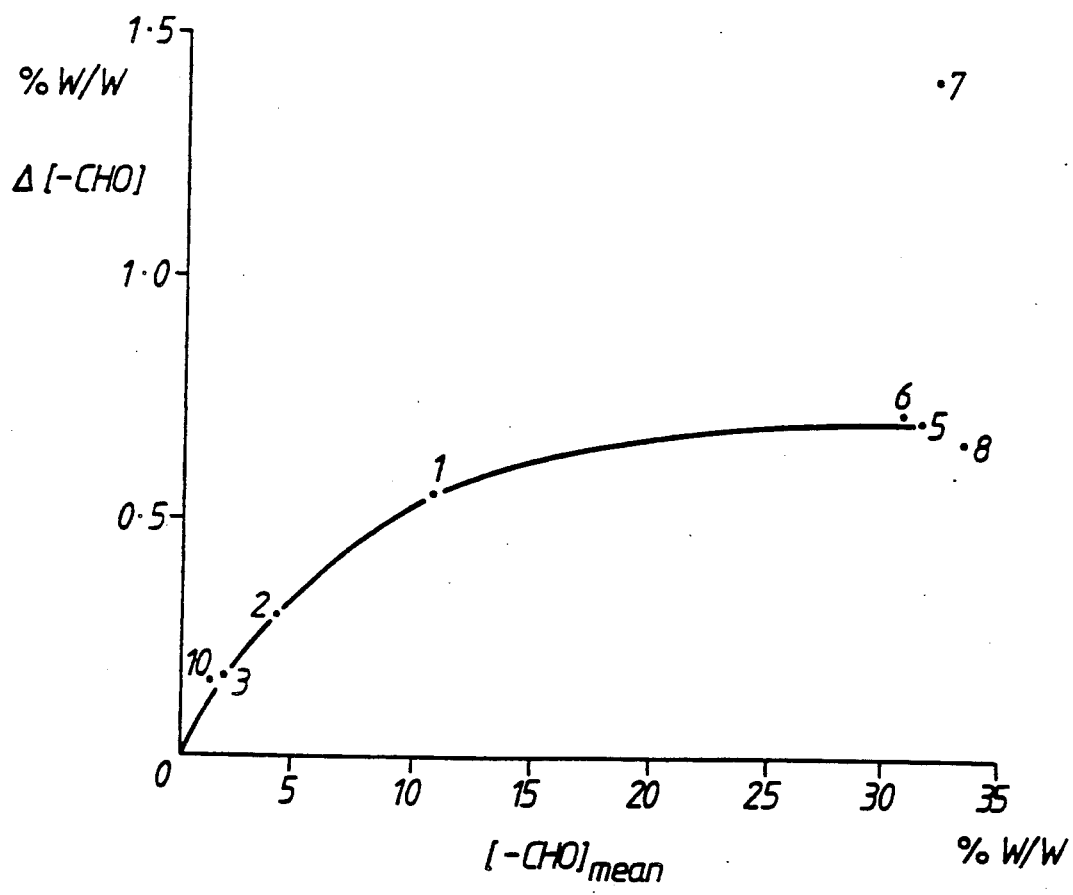
Figure 8:
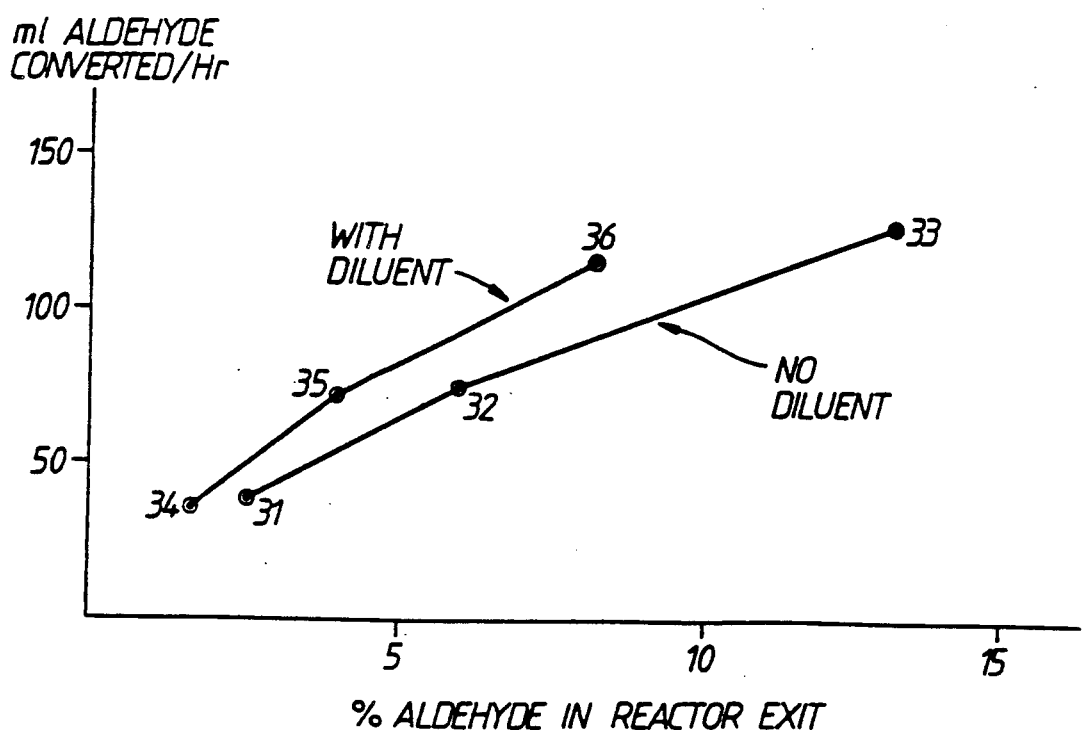
Figure 9:
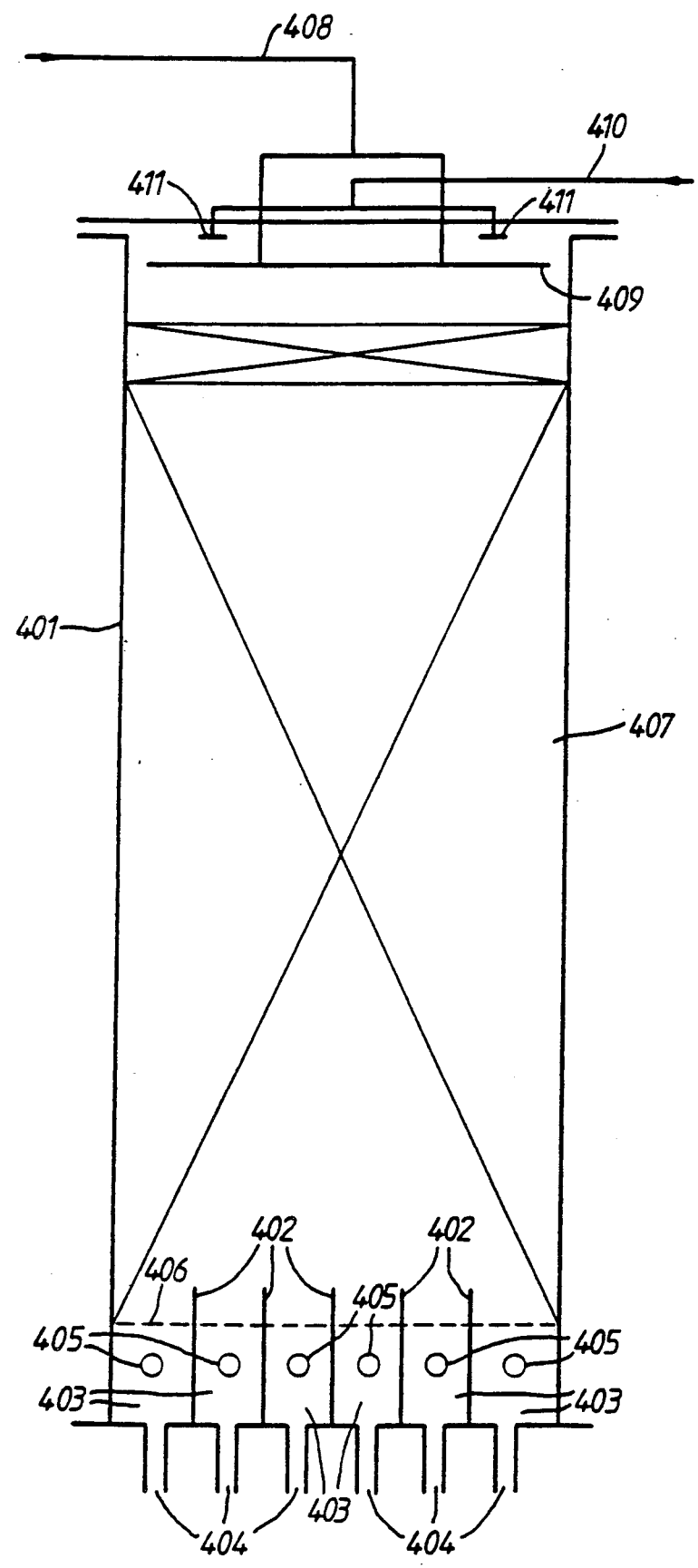
Figure 10:
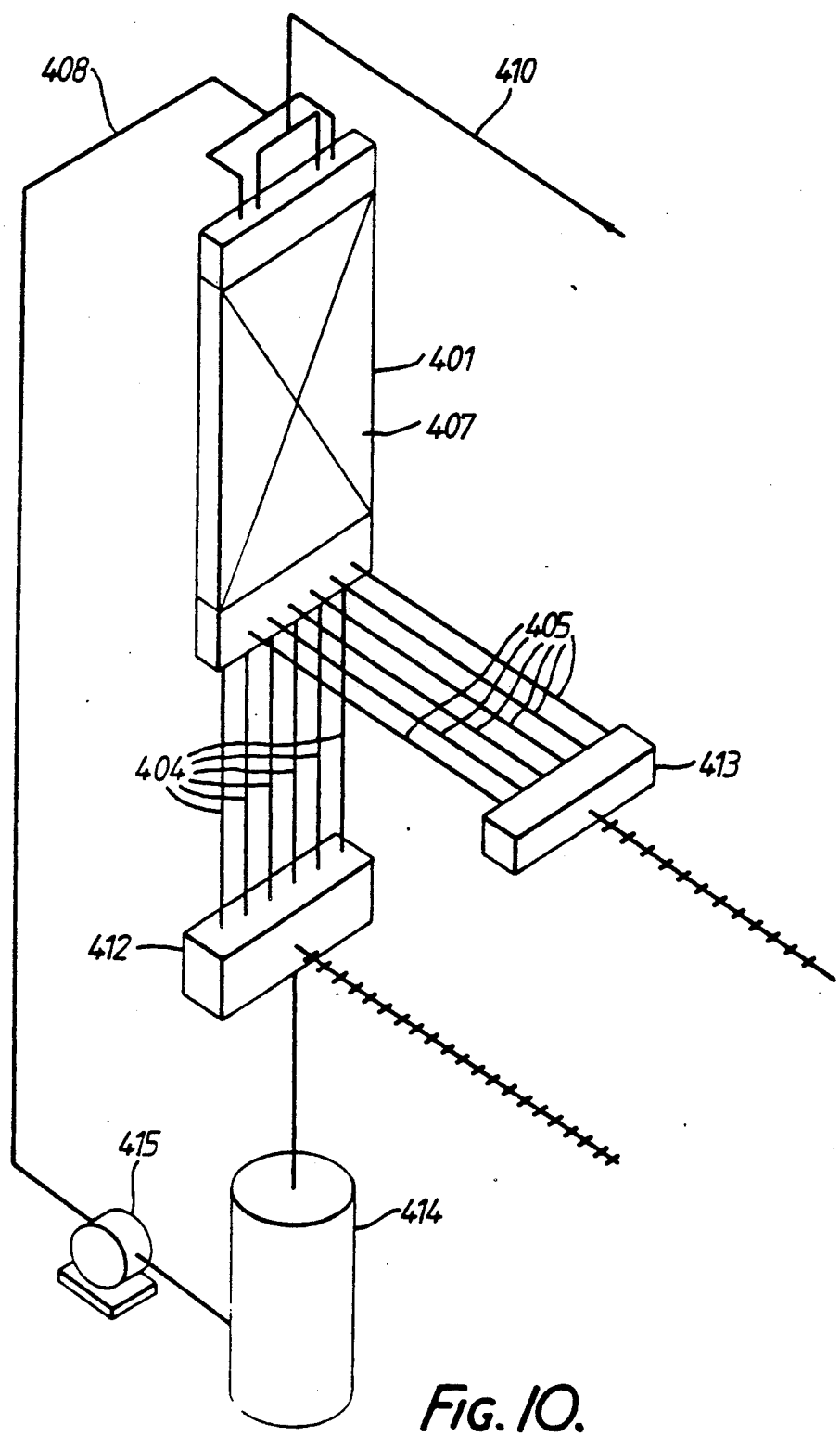
Figure 11:
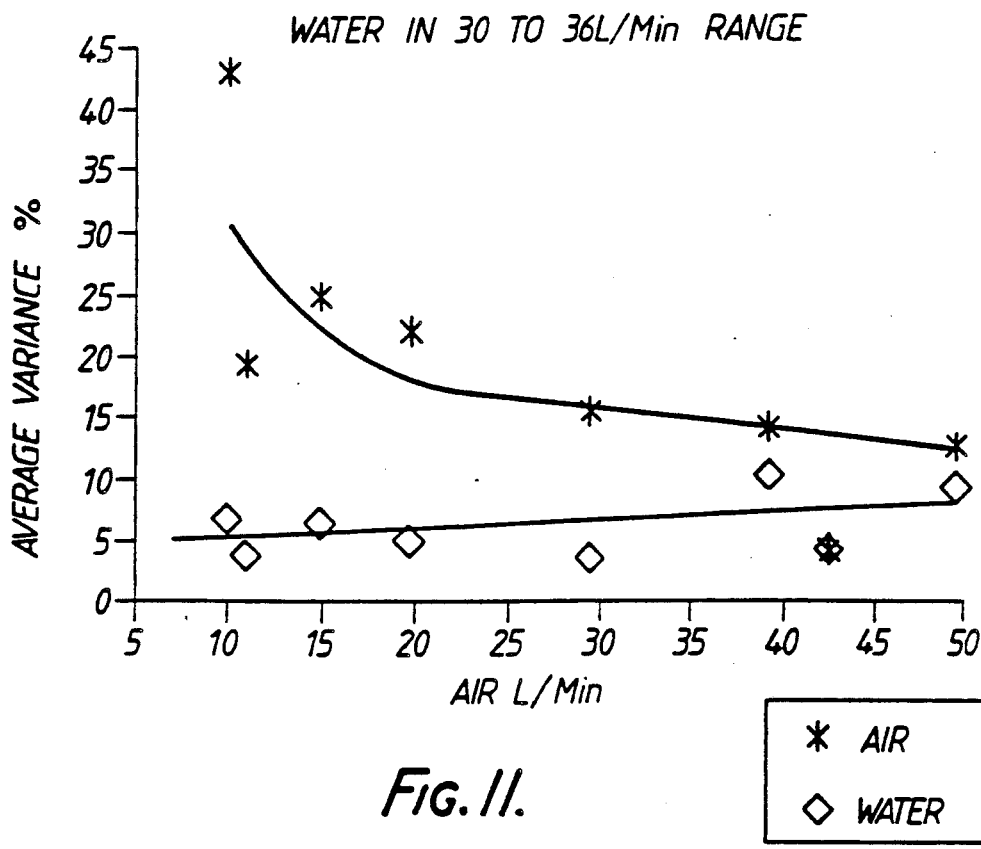
Figure 12:
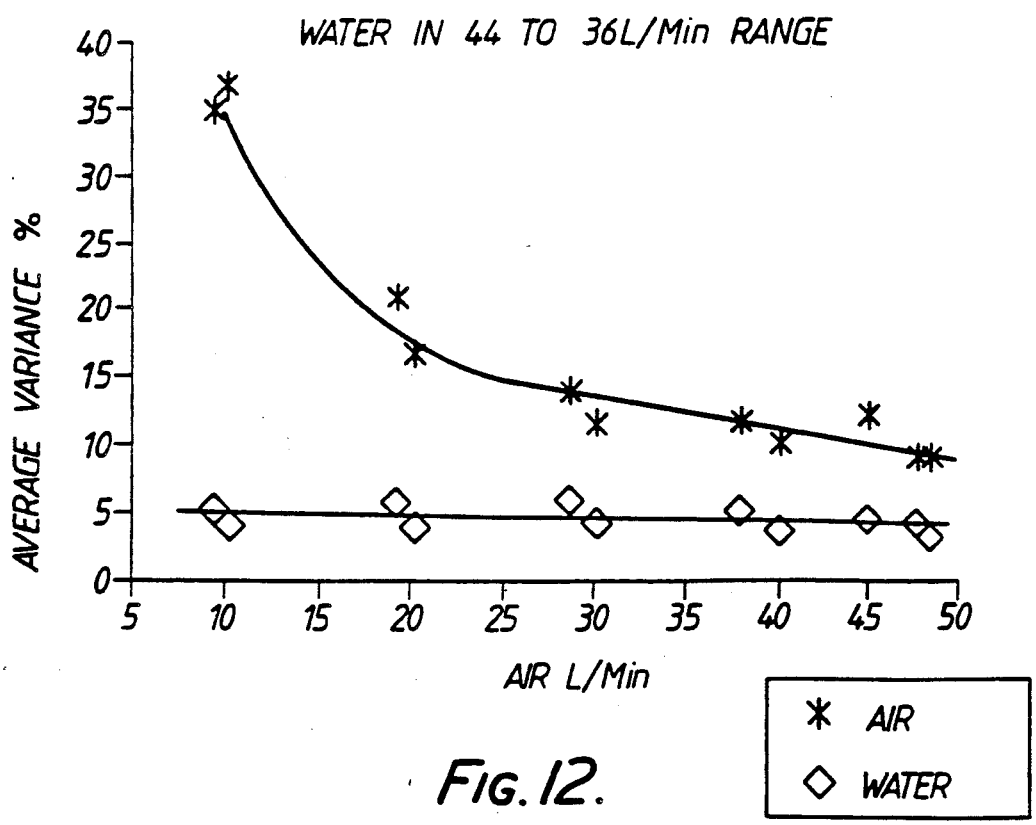
Figure 13:
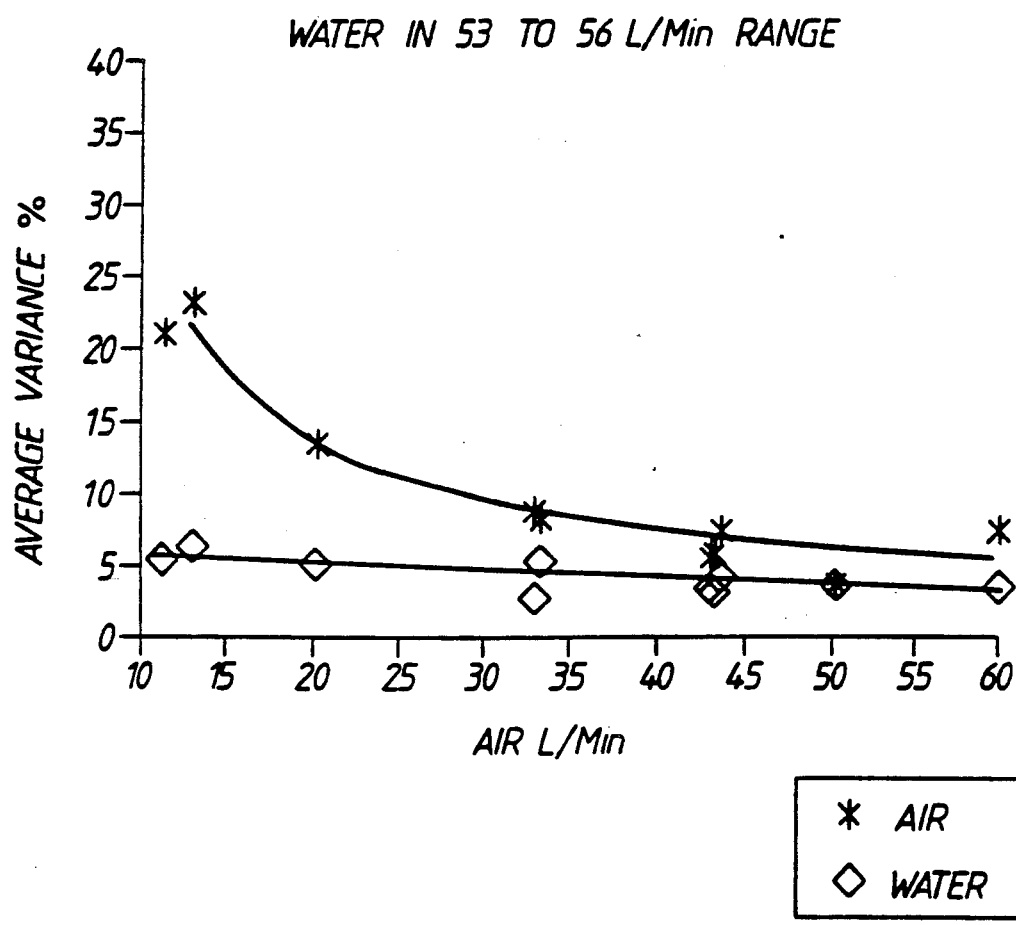

In order that the invention may be clearly understood and readily carried into effect five preferred processes in accordance therewith will now be described, by way of example only, with reference to FIGS. 1 to 5 of the accompanying drawings, each of which is a simplified flow diagram of a hydrogenation plant constructed in accordance with the invention, while FIG. 6 illustrates an experimental hydrogenation apparatus, FIGS. 7 and 8 plot data obtained from its use, FIGS. 9 and 10 illustrate a hydrodynamic test rig used to demonstrate the principles underlying the invention, and FIGS. 11 to 13 summarise data obtained from the rig of FIGS. 9 and 10.

It will be understood by those skilled in the art that FIGS. 1 to 5 are diagrammatic and that further items of equipment such as temperature and pressure sensors, pressure relief valves, control valves, level controllers and the like would additionally be required in a commercial plant. The provision of such ancillary items of equipment forms no part of the present invention and would be in accordance with conventional chemical engineering practice. Moreover it is not intended that the scope of the invention should be limited in any way by the precise methods of cooling and heating the various process streams, or by the arrangement of coolers, heaters, and heat exchangers, illustrated in FIGS. 1 to 5. Any other suitable arrangement of equipment fulfilling the requirements of the invention may be used in place of the illustrated equipment in accordance with normal chemical engineering techniques.

Referring to FIG. 1 of the drawings, a stainless steel reactor 1 is provided with an upper stainless steel grid 2 which supports an upper bed 3 of a granular aldehyde hydrogenation catalyst. This catalyst is a prereduced nickel on alumina catalyst in the form of 1/16 inch (1.6 mm) spheres containing 61% of nickel (calculated as metal) in the 50% reduced form and having a surface area of 140 m$^2$/g as measured by the so-called BET method.

Reactor 1 is of enlarged diameter at its lower end. This enlarged diameter lower end is fitted with a lower stainless steel grid 4 which supports a lower bed 5 of the same nickel catalyst. Thermocouples (not shown) are buried in catalyst beds 3 and 5 and reactor 1 is thermally insulated. Steam heating coils (not shown) are provided under the thermal insulation in order to assist in heating reactor 1 at start up.

Layers of open-celled honeycomb grid material (not shown) may be laid one on top of one another on top of grids 2 and 4 as the respective bed is loaded up with catalyst, each layer being offset from the layer below it so as to assist in even distribution of liquid over the entire bed and to avoid "channelling" of gas through the bed.

The space 6 below lower grid 4 is used to collect liquid emerging from the bottom of second bed 5. Such liquid is withdrawn by way of line 7 and is recycled by means of pump 8 and lines 9 and 10 through heat exchanger 11 and then through line 12 to a static liquid distributor 13 positioned above upper bed 3 at the top of reactor 1.

Reference numeral 14 indicates a feed line for heat exchanger 11 for supply of a heating medium (e.g. steam) or cooling water as need arises. Heat exchanger 11 can be bypassed by means of by pass line 15, flow through which is controlled by means of a valve 16 coupled to a temperature controller 17 which monitors the temperature in line 12. Aldehyde to be hydrogenated is supplied in line 18 and admixed with the liquid exiting heat exchanger 11. The resulting feed solution which typically contains about 10% w/w aldehyde is passed by way of line 12 to the top of catalyst bed 3 at a flow rate corresponding to a superficial liquid velocity down through the catalyst bed 3 of from about 1.5 cm/sec to about 3 cm/sec. A liquid intermediate reaction product containing typically less than about 1,000 ppm aldehyde emerges from the bottom of bed 3 at substantially the same rate as the flow rate in line 12 and passes down through catalyst bed 5. Because catalyst bed 5 is of larger diameter than bed 3 the superficial liquid velocity through bed 5 is less than that through bed 3, typically from about 0.25 cm/sec to about 1.0 cm/sec. Alcohol hydrogenation product is withdrawn by way of line 19 under the control of valve 20 which is itself controlled by means of a level controller 21 arranged to monitor the liquid level in bottom space 6 of reactor 1.

Hydrogen-containing gas from a pressure swing adsorption unit (not shown) is supplied to reactor 1 in line 22. A major part of the gas flows in line 23 to the top of reactor 1 under the control of a flow controller 24 whilst the remainder is fed by way of line 25 under the control of a further flow controller 26 to an upper part of the bottom space 6 at a point above the liquid level in bottom space 6. Flow controllers 24 and 26 are set so that the gas flow rate downwards through catalyst bed 3 at its upper face corresponds to a flow of hydrogen that is about 105% of the stoichiometric quantity of hydrogen required to hydrogenate to alcohol all the aldehyde supplied in line 18. Typically this corresponds to a superficial gas velocity at the upper surface of bed 3 in the range of from about 1 cm/sec to about 4 cm/sec. A minor amount only of gas flows in line 25, typically ranging from about 1% to about 5% of the flow rate in line 23.

A gas purge stream is taken from the space 27 between the two catalyst beds 3 and 5 in line 28. This is passed through a condenser 29 supplied with cooling water in line 30. Condensate is collected in drum 31 and is returned to reactor 1 in line 32. The resulting purge gas stream is taken in line 33 and passed through a further condenser 34 which is supplied with refrigerant in line 35. Pressure control valve 36 is used to control the pressure within the apparatus and hence the rate of withdrawal of purge gas in line 37.

Reference numeral 38 indicates a static liquid distributor for distributing evenly across the top of lower bed 5 liquid that exits upper bed 3. Line 39 and valve 40 are used for initial charging of the reactor 1 with liquid.

Reference numeral 41 indicates an optional internal cooling coil which is supplied with cooling water in line 42.

The use of honeycomb grid material in bed 5 which has been mentioned above is desirable as an upward flow of hydrogen containing gas is contacting a downflowing liquid; in this case there is a distinct tendency, in the absence of such honeycomb grid material, for the gas to flow up the central axis of the bed and for the liquid to flow down the walls. The use of honeycomb grid material or of a similar liquid flow distribution material within catalyst bed 5 helps to obviate this tendency and to promote proper countercurrent flow through bed 5.

Figure 2:
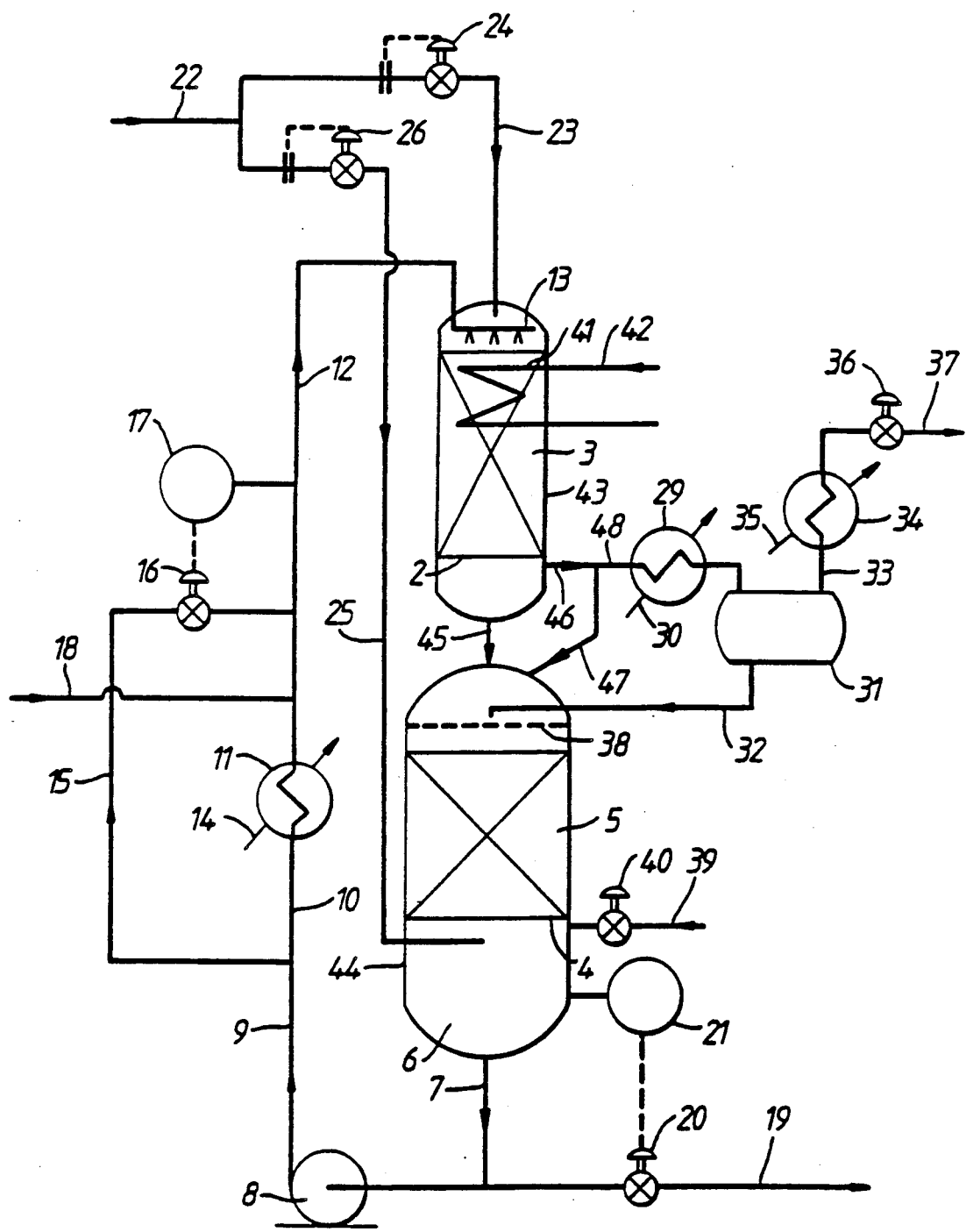

The plant of FIG. 2 is generally similar to that of FIG. 1 and like reference numerals have been used therein to indicate like features.

Instead of a single reactor vessel 1 the plant of FIG. 2 has two separate reactors 43, 44 each containing a respective catalyst bed 3, 5. Reactor 44 is of larger diameter than reactor 43. Liquid intermediate reaction product emerging from the bottom of first catalyst bed 3 collects in the bottom of reactor 43 and passes by way of line 45 to the top of reactor 44. Purge gas is taken from reactor 43 in line 46 and from reactor 44 in line 47 which joins line 46 to form line 48 which leads in turn to condenser 29. Condensate is returned via line 32 from drum 31 to the top of reactor 44.

The apparatus of FIG. 2 permits operation of the two reactors 43 and 44 at different pressures; in this case a valve (not shown) can be provided in one or both of lines 46 and 47 and a pump (not shown) can be provided, if necessary, in line 32.

Figure 3:
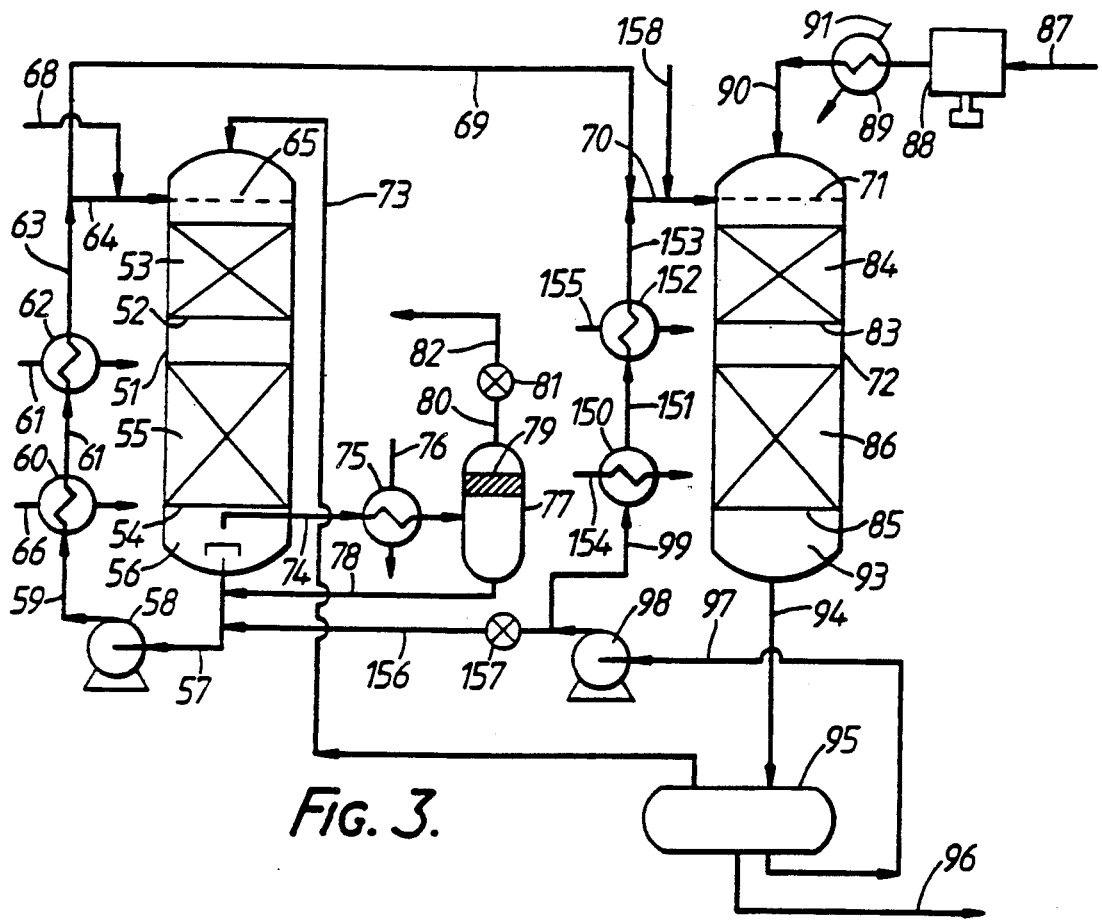

Referring to FIG. 3 of the drawings, a first reactor 51 is provided with an upper grid 52 which supports an upper bed 53 of a granular aldehyde hydrogenation catalyst. This catalyst is a prereduced nickel on alumina catalyst in the form of 1/16 inch (1.6 mm) spheres containing 61% of nickel (calculated as metal) in the 50% reduced form and having a surface area of 140 m$^2$/g as measured by the co-called BET method.

First reactor 51 is also fitted with a lower grid 54 which supports a lower bed 55 of the same nickel catalyst. Thermocouples (not shown) are buried in catalyst beds 53 and 55 and reactor 51 is thermally insulated. Steam heating coils (not shown) are provided under the thermal insulation in order to assist in heating reactor 51 at start up.

As in the case of the plant of FIG. 1, layers of honeycomb grid material can optionally be introduced into each bed of catalyst as beds 53 and 55 are loaded into the reactor 51 in order to assist in promoting even distribution of liquid throughout the respective bed in operation of the plant.

The space 56 below lower grid 54 is used to collect liquid emerging from the bottom of second bed 55. Such liquid is withdrawn by way of line 57 and is recycled by means of pump 58 and line 59 through heat exchanger 60. It is then fed through line 61 to a second heat exchanger 62 from which it is fed by way of lines 63, 64 to a static liquid distributor 65 positioned above upper bed 53 at the top of first reactor 51.

Reference numeral 66 indicates a feed line for heat exchanger 11 for supply of a heating medium (e.g. steam) or cooling water as need arises. Heat exchanger 62 is provided with a steam heating line 67. Aldehyde to be hydrogenated is supplied in line 68 and admixed with the liquid exiting heat exchanger 62. This is mainly product alcohol, but still contains a minor amount of hydrogenatable material. It acts as a diluent for the aldehyde. The rate of recycle in line 64 is selected so as to produce, upon admixture with the incoming aldehyde in line 68, a solution of aldehyde in the product alcohol which typically lies in the range of from about 5 mole % up to about 30 mole % and is selected such that the superficial liquid velocity down through catalyst beds 53 and 55 is in the range of from about 1.5 cm/sec to about 3 cm/sec.

Part of the recycle stream in line 63 is withdrawn by way of line 69 and is passed by way of line 70 to a static liquid distributor 71 fitted near the top of a second reactor 72.

Hydrogen-containing gas is supplied to first reactor 51 in line 73. The source of such hydrogen-containing gas will be described further below.

A gas purge stream is taken from the space 56 below catalyst bed 55 in line 74. This is passed through a condenser 75 supplied with cooling water in line 76. Condensate is collected in gas-liquid separator 77 and is returned to line 57 in line 78. Reference numeral 79 indicates a mist eliminator pad. The resulting purge gas stream is taken in line 80 and is passed through a vent valve 81 which is used to control the pressure within the apparatus and hence the rate of discharge of purge gas in line 82.

Second reactor 72 is provided with an upper grid 83 which supports an upper bed 84 of hydrogenation catalyst and with a lower grid 85 which supports a lower bed 86 of the same catalyst. The catalyst of beds 84 and 86 may be the same as that of beds 53 and 55. Layers of honeycomb grid material may optionally be included in beds 84 and 86 to assist in obtaining even liquid distribution therethrough.

Make up hydrogen-containing feed gas is supplied to the plant in line 87 from a pressure swing adsorption unit (not shown), is compressed (if necessary) by means of gas compressor 88 and is then passed by way of heat exchanger 89 and line 90 to the upper end of second reactor 72. Reference numeral 91 indicates a steam heating line. The gas from line 90 and the feed in line 70 flow in co-current downwardly through second reactor 72. The rate of supply of make up gas is controlled so as to correspond to about 105% of the stoichiometric quantity of hydrogen required to hydrogenate to product alcohol all of the aldehyde supplied in line 68 after allowance is made for dissolved hydrogen leaving the system in the product stream in line 96. This generally corresponds to a superficial velocity of gas entering the top of catalyst bed 84 in the range of from about 1 cm/sec to about 4 cm/sec. As the feed solution supplied in line 70 to second reactor 72 contains only traces of hydrogenatable organic material, very little hydrogen reacts in passage through beds 84 and 86. Substantially all of any hydrogenatable material remaining in the liquid in line 69 is hydrogenated in passage through second reactor 72. Hence what collects in the space 93 at the bottom of second reactor 72 below catalyst bed 86 is a mixture of hydrogen-containing gas and product alcohol. This is led in line 94 to a product recovery drum 95; hydrogen-containing gas therefrom is led by way of line 73 to the upper end of first reactor 51, as explained hereinabove. The gas flows into the top of catalyst bed 53 at a superficial velocity of from about 1 cm/sec to about 4 cm/sec. Liquid product alcohol which collects in drum 95 is recovered in line 96 and passed on for product purification in conventional manner, e.g. distillation in one or more fractional distillation stages.

Second reactor 72 can be operated, as described above, on a once-through basis as a single pass reactor. Alternatively the incoming intermediate reaction product in line 69 can be admixed with recycled product from product recovery drum 95. To this end a bypass line 97 is provided to enable recycle to be effected by means of recycle pump 98. This pumps crude liquid alcohol product by way of line 99 through heat exchanger 150 and then via line 151 to a further heat exchanger 152 for recycle in line 153 and admixture with intermediate reaction product in line 69. Reference numerals 154 and 155 indicate heating or cooling lines for heat exchangers 150 and 152 respectively, by means of which temperature control of the liquid supplied in line 70 can be controlled.

Pump 98 and heat exchangers 150 and 152 can be used at start up of the plant to warm up the catalyst beds 84 and 86 by circulating alcohol through reactor 72 prior to introduction of aldehyde to the plant. Heat exchangers 60 and 62 and pump 58 can be used in a similar way to circulate alcohol through reactor 51 and warm its catalyst beds 53 and 55 to the desired starting temperature.

Product alcohol can be supplied to reactor 51 from product recovery drum 95, using pump 98, by way of line 156 under the control of valve 157.

If desired, a secondary feed of aldehyde can be supplied by way of line 158, e.g. at start up of the plant.

The apparatus of FIG. 3 permits operation of the reactor 51 at a different lower pressure than reactor 72; in this case a pressure let down valve (not shown) can be provided in line 73 and a pump (not shown) can be provided in line 69. Alternatively reactor 72 can be operated at a lower pressure than reactor 51; in this case a compressor (not shown) is provided in line 73 and a valve (also not shown) in line 69.

Figure 4:
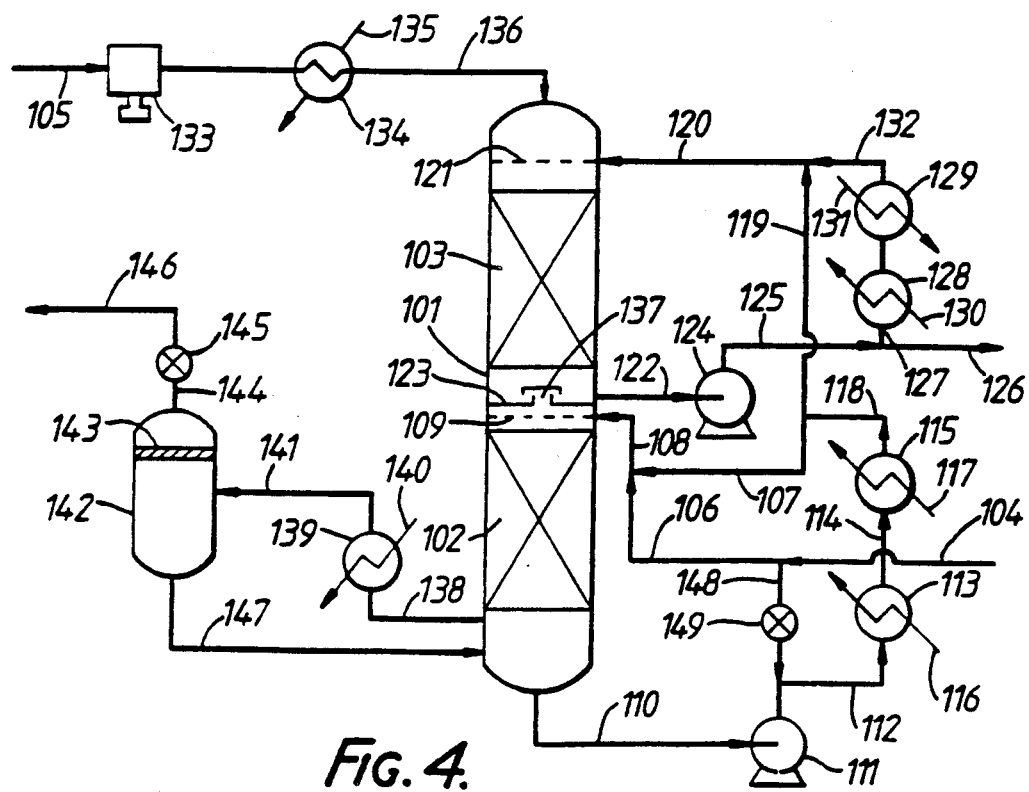

Instead of two reactor vessels 51 and 72 the plant of FIG. 4 has a single reactor 101 containing two hydrogenation catalyst beds 102 and 103. As with the plant of FIG. 3 each bed may optionally include layers of honeycomb grid material to assist in promoting even distribution of liquid throughout the bed and to avoid "channelling" of gas through the bed. Catalyst bed 102 constitutes a first hydrogenation zone and catalyst bed 103 a second hydrogenation zone. Aldehyde to be hydrogenated is supplied in line 104 and hydrogen-containing feed gas is supplied from a pressure swing adsorption unit (not shown) in line 105 in an amount corresponding to about 105% of the stoichiometric quantity of hydrogen required to hydrogenate all of the aldehyde supplied in line 104 to product alcohol.

The aldehyde feed flows from line 104 in line 106 and is admixed with a recycled alcohol stream in line 107. The admixed stream, containing typically from about 5 mole % to about 30 mole % aldehyde in a predominantly alcohol diluent, is fed in line 108 to a static liquid distributor 109 above catalyst bed 102. The flow rate is sufficient to correspond to a superficial liquid velocity down catalyst bed 102 of from about 1.5 cm/sec to about 3 cm/sec. Intermediate reaction product is collected at the bottom of reactor 101 and is pumped by way of line 110, pump 111 and line 112 to a heat exchanger 113. Then the liquid intermediate reaction product, which contains typically from about 0.1 mole % to about 5 mole % chemically unsaturated hydrogenatable organic material, is fed in line 114 to a further heat exchanger 115. Reference numeral 116 and 117 indicate respective heating or cooling lines for heat exchangers 113 and 115. The liquid intermediate reaction product in line 118 is fed in part in line 107 as the recycle stream to catalyst bed 102 and in part via lines 119 and 120 to a further static liquid distributor 121 fitted above catalyst bed 103. Again, the superficial liquid velocity of the liquid flowing into catalyst bed 103 is from about 1.5 cm/sec to about 3 cm/sec.

The chemically unsaturated hydrogenatable organic material remaining in the intermediate reaction product is substantially all hydrogenated to product alcohol in passage through catalyst bed 103. Substantially pure alcohol is recovered in line 122 from chimney tray 123 and is pumped by means of pump 124 and lines 125 and 126 to a conventional alcohol purification section (not shown). If desired, part of the product alcohol can be passed by way of line 127 through heat exchangers 128 and 129, whose heating or cooling lines are indicated at 130 and 131 respectively, to line 132 for recycle to liquid distributor 121.

The hydrogen-containing feed gas in line 105 is compressed as necessary by means of gas compressor 133, heated in heat exchanger 134, whose steam heating line is indicated at 135, and supplied in line 136 to the top of reactor 101 above catalyst bed 103 at a rate corresponding to a superficial gas velocity at the upper surface of catalyst bed 103 of from about 1 cm/sec to about 4 cm/sec. Gas emerging from the bottom of catalyst bed 103 passes through an orifice 137 in chimney tray 123 and into catalyst bed 102. As very little hydrogen is consumed in passage through bed 103 the superficial gas velocity at the upper surface of catalyst bed 102 is similarly in the range of from about 1 cm/sec to about 4 cm/sec. A purge gas stream is taken from the bottom of reactor 101 below catalyst bed 102 in line 138 and is passed through a condenser 139 which is supplied with cooling water in line 140. The cooled gas is passed in line 141 to a gas-liquid separator 142 which is fitted with a spray eliminator pad 143. The purge gas passes out in line 144 through control valve 145 to a vent line 146. The condensate is returned from gas-liquid separator 142 to reactor 101 in line 147. Reference numerals 148 and 149 represent a bypass line and bypass valve respectively for use at start up of the plant.

Typical operating conditions in the plants of FIGS. 1 to 4 include use of an inlet temperature to each catalyst bed in the range of from about 100° C. to about 130° C. and a pressure of from about 5 bar to about 50 bar. In each case the concentration of aldehyde in the feed solution to each catalyst bed is such as to produce an adiabatic temperature rise across each bed of no more than about 20° C.

FIG. 5 illustrates a modified form of plant in which an added diluent is used. This form of plant is useful, for example, in the case in which the presence of an added adjuvant is desirable, such as ammonia in the hydrogenation of a nitro compound (e.g. nitrobenzene).

Material to be hydrogenated, such as nitrobenzene, is supplied in line 201 to a mixing device 202 to which is also fed in line 203 a mixture of make up diluent and adjuvant, such as a solution of ammonia in ethanol (containing some water), from line 204 as well as recycled diluent/adjuvant mixture in line 205. The resulting dilute nitrobenzene solution is fed to heater 206 in line 207 and admixed with make up hydrogen in line 208. Reference numeral 209 indicates a steam heating line for heater 206. The mixture of hydrogen, nitrobenzene, ammonia and ethanol flows in line 210 to hydrogenation zone 211. This can be a single reactor or a pair of reactors as used in the plant of one of FIGS. 1 to 4. As with the plants of FIGS. 1 to 4 layers of open-celled honeycomb material can be incorporated into the, or into each, catalyst bed of hydrogenation zone 211 in order to promote even co-current flow of liquid and gas downward through the bed. The liquid flow rate in line 207 is controlled so as to provide a superficial liquid velocity down through the or each bed of catalyst of from about 1.5 cm/sec to about 3 cm/sec, whilst the gas flow rate in line 208 is adjusted to provide at the operating pressure and temperature of the plant an amount of hydrogen equivalent to 115% of the stoichiometrically required amount. A mixture of a hydrogen-depleted purge gas and of an ethanolic aniline solution, which contains ammonia and water produced by the hydrogenation reaction, is recovered from the bottom of hydrogenation zone 211 in line 212. This is fed to a gas liquid separator 213. Gas is purged from the plant in line 214 under the control of valve 215. A cooler 216 is supplied with cooling water in line 217 in order to trap volatile materials. The liquid phase is led in line 218 to a distillation column 219 from which a mixture of ammonia, water and ethanol is recovered overhead in line 220 and is condensed by means of condenser 221. The resulting condensate collects in drum 222; part is returned to column 219 in line 223 as a reflux stream whilst the rest is recycled in line 224 by means of pump 225 to form the recycle stream in line 205. Reference numeral 226 indicates a gas vent line to condensate drum 222, whilst reference numeral 227 indicates the cooling water supply line for condenser 221. The bottom product from column 219 in line 228 consists of substantially nitrobenzene-free aniline containing a minor amount of ethanol and water produced in the reaction. Part is recycled to column 219 by way of line 229 and column reboiler 230 whose steam supply line is indicated at 231. The remainder is passed on for further purification and storage in line 232.

In a variant of the plant of FIG. 5 mixing device 202 is omitted and lines 201 and 204 are connected to line 224 upstream from pump 225 which then serves as a mixing device.

The invention is further illustrated with reference to the following Examples. Examples 7 and 9 are Comparative Examples and do not illustrate the invention.

EXAMPLES 1 TO 11

The hydrogenation of a $C_{13}$ aldehyde stream containing 69.98 wt % n-tridecanal, 5.70 wt % 2-methyldodecanal, 0.30 wt % of heavy by-products resulting from aldehyde self condensation reactions and the balance $C_{12}$ aliphatic hydrocarbons, was studied in the apparatus depicted in FIG. 6. This included a reactor 301 made of stainless steel tubing, 2.54 cm internal diameter and 91.4 cm in length, arranged with its axis vertical and fitted with an annular jacket 302 through which hot oil from a thermostatically controlled bath could be circulated. Reactor 301 contained a bed 303 of catalyst supported on a layer 304 of 1.6 mm diameter glass beads 2 cm deep which was itself supported on a stainless steel mesh grid 305 some 10 cm above the base of reactor 301. The volume of catalyst bed 303 was 52.3 ml and the catalyst was a pre-reduced and air stabilised nickel on alumina catalyst containing 61% w/w of nickel (calculated as metal) in the 50% reduced form and having a surface area of 140 m$^2$/g as measured by the so-called BET method. The physical form of the catalyst was near spherical granules of a nominal 1/16 inch (1.6 mm) diameter; the actual size range limits of the particles was from 1.4 mm to 2.36 mm as determined by sieve analysis. The upper portion of reactor 301 was filled with a layer 306 of 1.6 mm diameter glass beads; this layer 306 ensured that the temperature of the feed solution and entrained hydrogen supplied to catalyst bed 303 could be controlled to a preselected value.

Reactor 301 was also fitted with a thermocouple pocket 307 of small diameter for a thermocouple 308. During the packing procedure it was determined that the depth of catalyst bed 303 was 10.5 cm. Liquid could be withdrawn from the bottom of reactor 301 in line 309 by means of pump 310 and recycled to the top of reactor 301 in line 311. The rate of recycle of liquid in line 311 could be measured using a mass flow meter (not shown). Aldehyde feed could be supplied to the apparatus from a burette (not shown) in line 312 by means of a feed pump (not shown). Hydrogen could be supplied from a storage cylinder via a pressure let down valve and a flow controller (neither of which is shown) in line 313. A mixture of gas and liquid could also be withdrawn from reactor 301 by means of an overflow pipe 314 and passed in line 315 to a gas/liquid separation vessel 316. Pressure control valve 317 allowed a purge gas stream to be let down to atmospheric pressure and passed in line 318 to a wet gas meter (not shown) before being vented to the atmosphere. Liquid product could be removed from the system in line 319 by means of a pressure let down valve 320 operating under the influence of a liquid level controller 321. Samples of this liquid product were analysed by gas-liquid chromatography from time to time. Such analysis was repeated after any change in operating conditions had been effected until the results showed that steady state conditions had been re-established. The whole apparatus was positioned in a fume cupboard supplied with warm air at 40° C. to eliminate any danger of blockage of lines due to solidification of n-tridecanol (m.p. 32–33° C.).

After purging the apparatus with nitrogen approximately 120 ml of $C_{13}$ alcohol were charged to the apparatus by means of line 312, the circulating hot oil flow was established at a temperature of 120° C., and pump 310 was set into operation. This quantity of liquid was sufficient to fill the bottom of reactor 301. A flow of hydrogen was established through the apparatus and then the system was brought up to operating pressure and the aldehyde feed pump started. The results are listed in Table 1. All Examples were carried out using circulating oil at 120° C. and in each case, except Example 7 and especially Example 9 when thermocouple 308 indicated an incipient temperature runaway, the temperature of the catalyst bed 303 remained within 5° C. of 120° C. H₂ flow rates are measured in "normal" liters per hour (i.e. liters of gas at 0° C. and 1 bar).

TABLE 1

| Example No. | Aldehyde feed rate (ml/hr) | H₂ feed rate (l/hr) | H₂ purge rate (l/hr) | Liquid Recycle rate (l/hr) | SLV (cm/sec) | Bed Temp. (°C.) | % n-aldehyde in reactor effluent (w/w) | % "heavies" in reactor effluent (w/w) |
|---|---|---|---|---|---|---|---|---|
| 1 | 240 | 38.7 | 19.8 | 25.8 | 1.58 | 124.5 | 10.3 | 2.98 |
| 2 | 120 | 31.4 | 19.8 | 25.8 | 1.57 | 123.9 | 4.26 | 1.36 |
| 3 | 60 | 26.7 | 19.8 | 25.8 | 1.57 | 123.1 | 1.86 | 1.18 |
| 4 | 30 | 23.9 | 19.8 | 25.8 | 1.57 | 123.0 | 0.94 | 1.08 |
| 5 | 480 | 41.9 | 19.8 | 25.8 | 1.59 | 124.7 | 31.2 | 6.15 |
| 6 | 480 | 62.8 | 39.5 | 25.8 | 1.59 | 125.0 | 30.4 | 6.26 |
| 7 | 480 | 42.5 | 19.8 | 13.0 | 0.82 | 131.2 | 31.3 | 6.76 |
| 8 | 480 | 24.9 | 3.9 | 25.8 | 1.59 | 124.8 | 33.6 | 6.38 |
| 9 | 480 | 45.5 | 19.8 | 5.1 | 0.34 | 143.9 | 26.3 | 6.82 |
| 10 | 60 | 27.1 | 19.8 | 25.8 | 1.57 | 123.3 | 1.56 | 1.44 |

Note: The term "SLV" means superficial liquid velocity and is calculated assuming a density of 0.75 g/cc at reactor inlet conditions and 0.83 g/cc at room temperature for the reactor inlet feed solution As the recycle rate in line 311 is known and the n-aldehyde concentration, i.e. $[-CHO]_{exit}$, in the liquid being recycled is also known and as the feed rate and aldehyde concentration in the material supplied in line 312 are also known, it is readily possible to calculate the n-aldehyde inlet feed concentration, i.e. $[-CHO]_{inlet}$, for each Example. From these figures was calculated, in each case, the mean n-aldehyde concentration, i.e. $[-CHO]_{mean}$, in the reactor, according to the equation:

$$[-CHO]_{mean} = \frac{[-CHO]_{inlet} + [-CHO]_{exit}}{2}$$

The mean n-aldehyde concentration is tabulated in Table 2 against the percentage change in n-aldehyde concentration $\{\Delta[-CHO]\}$ from one end of the reactor to the other. These data observations are plotted in FIG. 7.

TABLE 2

| Example No. | $[-CHO]_{mean}$ (% w/w) | $\Delta [-CHO]$ (% w/w) | Liquid recycle rate (l/hr) |
|---|---|---|---|
| 1 | 10.58 | 0.55 | 25.8 |
| 2 | 4.41 | 0.30 | 25.8 |
| 3 | 1.94 | 0.16 | 25.8 |
| 4 | 0.98 | 0.08 | 25.8 |
| 5 | 31.56 | 0.71 | 25.8 |
| 6 | 30.76 | 0.72 | 25.8 |
| 7 | 31.99 | 1.38 | 13.0 |
| 8 | 33.93 | 0.66 | 25.8 |
| 9 | 28.18 | 3.76 | 5.1 |
| 10 | 1.64 | 0.16 | 25.8 |

Examples 1 to 5 and 10 were all carried out with a liquid recycle rate of 25.8 l/hr and a hydrogen purge rate of 19.8 l/hr so that these data define the relationship between the amount of n-aldehyde converted in passage through reactor 301, i.e. $\Delta[-CHO]$, and the n-aldehyde concentration, $[-CHO]_{mean}$, within the reactor 301 under these conditions of hydrogen flow and liquid recycle rate. A considerable reduction in hydrogen purge flow rate to 3.9 l/hr makes very little difference to the amount of n-aldehyde converted in passage through reactor 301, i.e. $\Delta[-CHO]$, as can be seen by comparison of Examples 5 and 8. A large increase in hydrogen purge flow rate to 39.5 l/hr makes very little difference to the amount of n-aldehyde converted in passage through reactor 301, i.e. $\Delta[-CHO]$, as is readily apparent by comparison of Examples 5 and 6. In contrast a reduction in liquid recycle rate, although increasing the conversion of n-aldehyde in passage through reactor 301, i.e. $\Delta[-CHO]$, as shown by Examples 7 and 9, caused a marked increase in catalyst bed temperature, as detected by thermocouple 308, despite the use of circulating oil at 120° C. in jacket 302. This incipient temperature runaway was further accompanied by an increase in "heavies" formation.

The data defining the curve of FIG. 7 represent a scan of different horizontal segments of catalyst in a large reactor and can be used to calculate the depth of catalyst bed required for a commercial rector operating under appropriate conditions including aldehyde concentration, flow rate and temperature according to the teachings of the invention.

Comparison of the relative amounts of aldehyde converted over the reactor system calculated from the flow rates and aldehyde concentration changes across the reactor in Examples 7 and 9, using Example 5 as a reference, shows that virtually the same amount of aldehyde is converted in the reactor system in Example 7 as in Example 5, despite a significant increase in catalyst temperature and some increase in heavy by-products production. Comparison of Examples 5 and 9 show that an increase of only about 12% in aldehyde conversion by the reactor system has been gained at the expense of an unacceptable temperature rise and increase in heavy by-products formation. Example 9 in some measure represents the situation arising in a "local low flow volume element" of a large catalyst bed operated at low superficial liquid velocities. These comparisons illustrate that the space time productivity of the catalyst is maintained at high liquid superficial velocities and that potentially dangerous temperature excursions with consequent loss of catalyst activity and selectivity are obviated using the process of the invention.

EXAMPLES 11 TO 36

The apparatus of FIG. 6 was charged with 58 ml of the same catalyst and was used to investigate further the hydrogenation of the same C₁₃ aldehyde feedstock that was used in Examples 1 to 11. The reaction conditions and the results obtained are summarised in Table 3. In Examples 34 to 36 the C₁₃ aldehyde feedstock was diluted with n-tetradecane. In each case the liquid recycle rate was maintained at 28 l/hr, thus ensuring that the superficial linear liquid velocity through the reactor was at least 1.5 cm/sec.

FIG. 8 summarises the results of Examples 31 to 36. This is a graph of the amount of aldehyde converted per hour in the apparatus plotted against the concentration of aldehyde in the liquid phase exiting the reactor. The numerals on the graph indicate the numbers of the respective Examples. It will be seen that two separate curves can be plotted, one representing the data obtained when no diluent (i.e. n-tetradecane) has been added and the other when a diluent is used.

TABLE 3

| Example No. | Reactor Pressure (bar) | Aldehyde Feed Rate (l/hr) | n-tetradecane added (l/hr) | H$_2$ Exit Flow (l/hr) | Reactor Bed Temp. (°C.) | % n-aldehyde in reactor effluent (w/w) | % "heavies" in reactor effluent (w/w) |
|---|---|---|---|---|---|---|---|
| 11 | 18.24 | 0.06 | — | 63 | 122.5 | 1.93 | 3.22 |
| 12 | 18.24 | 0.24 | — | 254 | 123.4 | 11.58 | 5.79 |
| 13 | 25.13 | 0.24 | — | 254 | 123.4 | 10.34 | 5.13 |
| 14 | 25.13 | 0.12 | — | 109 | 122.6 | 4.69 | 4.34 |
| 15 | 25.13 | 0.12 | — | 86 | 133.2 | 3.14 | 3.70 |
| 16 | 25.13 | 0.24 | — | 176 | 133.7 | 7.65 | 5.01 |
| 17 | 18.24 | 0.24 | — | 193 | 134.1 | 8.64 | 6.56 |
| 18 | 18.24 | 0.12 | — | 100 | 133.3 | 3.75 | 5.16 |
| 19 | 21.68 | 0.18 | — | 150 | 128.8 | 6.96 | 5.44 |
| 20 | 21.68 | 0.12 | — | 107 | 128.4 | 4.26 | 4.82 |
| 21 | 21.68 | 0.24 | — | 223 | 129.0 | 10.07 | 6.16 |
| 22 | 25.13 | 0.18 | — | 140 | 133.6 | 5.86 | 5.41 |
| 23 | 25.13 | 0.18 | — | 183 | 123.1 | 8.52 | 5.79 |
| 24 | 18.24 | 0.18 | — | 206 | 123.2 | 9.37 | 7.08 |
| 25 | 18.24 | 0.18 | — | 160 | 133.5 | 6.91 | 6.74 |
| 26 | 18.24 | 0.06 | — | 57 | 132.6 | 1.80 | 5.07 |
| 27 | 25.13 | 0.06 | — | 57 | 132.6 | 1.58 | 4.26 |
| 28 | 18.24 | 0.12 | — | 140 | 124.1 | 5.93 | 6.35 |
| 29 | 18.24 | 0.06 | — | 73 | 123.9 | 2.51 | 5.22 |
| 30 | 18.24 | 0.24 | — | 280 | 124.6 | 13.18 | 8.00 |
| 31 | 18.24 | 0.06 | — | 73 | 124 | 2.65 | 5.22 |
| 32 | 18.24 | 0.12 | — | 140 | 124 | 6.07 | 6.35 |
| 33 | 18.24 | 0.24 | — | 280 | 124 | 13.32 | 8.00 |
| 34 | 18.24 | 0.06 | 0.06 | 57 | 124 | 1.75 | 2.75 |
| 35 | 18.24 | 0.12 | 0.12 | 90 | 124 | 4.08 | 3.21 |
| 36 | 18.24 | 0.24 | 0.24 | 177 | 124 | 8.43 | 3.90 |

Regression analysis of the rate of conversion ($R_N$) of n-aldehyde to products (expressed as gm moles of $C_{13}$ aldehyde converted/liter of catalyst/hr) produced an equation of the following form.

$$R_N = \frac{A \cdot e^{E/T^\circ K} \cdot RxBar^a \cdot \% NALD^b \cdot ALH_2^c}{\% HVY^d}$$

where $R_N$ = gm moles of n-aldehyde hydrogenated to products/liter of catalyst/hr $T^\circ K$ = average catalyst and temperature RxBar = Reactor pressure (bar)

%NALD = Mean % n-aldehyde in reactor (calculated)

$ALH_2$ = Calculated actual liters/hr of hydrogen exiting from the bottom of the catalyst bed at reactor pressure and temperature %HVY = % "heavies" in the reactor exit stream

| Coefficient | Standard Error of Coefficient |
|---|---|
| a = 0.156 | 0.122 |
| E = −4867.78 | 255.6 |
| b = 0.837 | 0.0867 |
| c = 0.0179 | 0.111 |
| d = 0.4497 | 0.0356 |
| A is a constant = | 345756 |
| e = the base for natural logarithms | (i.e. 2.71828 ...) |

The validity of the above rate equation is shown in Table 4 where predicted rates versus actual rates, in gm moles/l catalyst/hr, are compared.

TABLE 4

| Example No. | Observed Rate | Rate Predicted by Rate Equation |
|---|---|---|
| 11 | 2.99 | 2.82 |
| 12 | 10.15 | 9.77 |
| 13 | 10.33 | 10.12 |
| 14 | 5.61 | 5.44 |
| 15 | 5.80 | 5.86 |
| 16 | 10.71 | 10.88 |
| 17 | 10.71 | 10.34 |
| 18 | 5.80 | 5.56 |
| 19 | 8.25 | 8.14 |
| 20 | 5.61 | 5.62 |
| 21 | 10.33 | 10.58 |
| 22 | 8.25 | 8.38 |
| 23 | 8.06 | 8.02 |
| 24 | 7.87 | 7.62 |
| 25 | 8.25 | 8.28 |
| 26 | 3.00 | 2.95 |
| 27 | 3.00 | 3.01 |
| 28 | 5.61 | 5.60 |
| 29 | 2.99 | 2.94 |
| 30 | 9.77 | 10.06 |
| 31 | 2.92 | 3.13 |
| 32 | 5.54 | 5.69 |
| 33 | 9.81 | 9.98 |
| 34 | 2.88 | 2.93 |
| 35 | 5.35 | 5.55 |
| 36 | 9.20 | 9.40 |

This analysis of Examples 11 to 36 shows that:

(a) Hydrogen flow has little or no positive effect on the rate of hydrogenation under these liquid flow velocity conditions;

(b) Reactor pressure (i.e. hydrogen pressure) has a minor positive effect on the reaction rate and is of poor statistical significance (over the pressure range used 18.24 to 25.13 bar); and (c) "Heavies" are catalyst inhibitors.

These conclusions substantiate in a more rigorous way the insensitivity of the reaction kinetics to the rate of hydrogen passing through the catalyst bed which can be noted from comparison of Examples 5 and 6 and of Examples 5 and 8. Also the rate equation describes the effect of the process conditions on the catalyst in a differential manner; suitable integration of the equation over the depth of a commercial catalyst bed will provide a valuable prediction of the bed's performance.

The plants of FIGS. 1 to 5 and the operating techniques described above are generally applicable to hydrogenation of organic materials. It will accordingly be readily apparent to the skilled reader that the teachings of the invention can be practised with a wide variety of hydrogenation reactions other than the aldehyde hydrogenation reaction specifically described in relation to FIGS. 1 to 4 of the accompanying drawings and the nitrobenzene hydrogenation reaction described in relation to FIG. 5 of the drawings.

EXAMPLE 37

Examples 1 to 36 used experimental systems where reactors of small diameter (2.54 cm) were used. Commercial reactors of much larger diameter are necessary in order to achieve the necessary production rates. Therefore the distribution of gas and liquid passing in co-current downflow through a much larger bed of particulate solid was investigated in an apparatus which is illustrated in FIGS. 9 and 10. This comprises a rectangular section column 401 which was constructed from 1.25 mm thick "Perspex" (Registered Trade Mark) sheet so as to enable its contents to be viewed. Partitions 402 near its base divided the base of the column 401 into six bays 403, each of which had a corresponding outlet line 404 for water and an outlet line 405 for air. Reference numeral 406 indicates a perforated support for a bed 407 of particles intended to simulate a hydrogenation catalyst. Bed 407 consisted of impervious ceramic balls of nominal size 2.4 to b 4 mm, more than 80% of which were 3 mm or less in diameter. Water was supplied in line 408 to a bar distributor 409 above the top of the bed 407, whilst air was fed in line 410 from a compressor (not shown) to inlets 411 at the top of column 401. Bed 407 measured approximately 460 mm × 75 mm × 1,425 mm and was topped with a layer of 12.7 mm diameter polypropylene balls approximately 200 mm deep which was intended to enhance the uniformity of distribution of the water over the top of bed 407. The water that was collected in each bay 403 was conducted along a line 404 of standard length to a corresponding turbine meter in a bank 412 of turbine meters, each receiving water from a respective bay 403. Similarly air from each bay 403 was conducted along a line 405 of standard length to a corresponding turbine meter in a bank 413 of such turbine meters, each receiving air from a respective bay 403. As indicated by reference numerals 414 and 415 the signals from the two banks of meters 412 and 413 were transmitted to respective data loggers (not shown). By providing lines 404 of essentially identical length and diameter for water and lines 405 similarly of essentially identical length and diameter for the air flow from each bay 403 it was ensured that, so far as possible, the risk of the air and water flow measurement systems interfering with the measurements of flow through the bed 407 was avoided. However, at low air flow rates, of the order 2 to 3 liters per minute, the air flow measurement turbines of bank 413 became inaccurate and/or inoperative. Accordingly the corresponding air distribution measurements have no significance in this low air flow range. From the meters of bank 412 the water was collected in a tank 414 and recirculated to the top of the apparatus by pump 415.

Measurements were made with water flow rates in line 408 of 30 to 55 liters per minute and air flow rates in line 410 of 59 to 5 liters per minute. These flow rates were chosen to simulate a range of flow rates likely to be encountered in a commercial hydrogenation reactor operated in accordance with the teachings of this invention and correspond to a liquid phase superficial velocity of 1.43 to 2.63 cm/sec and a gas phase superficial velocity of 0.096 to 2.01 cm/sec.

The distribution of fluid across the bed 407 was calculated as follows:

For each fluid:
Average flow = sum of flows/6
Variance = [Average flow − measured flow]
Average variance = sum of variances/6

(It should be noted that the variance was always recorded as a positive number).

The results are recorded in Tables 5 to 7 and plotted in FIGS. 11 to 13.

At the higher gas and liquid flow rates the operation of a highly dispersed gas/liquid regime was clearly shown.

In those cases where active liquid/air bubble movement was visually observable no static regions of the bed were evident; the phase in a given bed void was replaced by the other phase at apparently random intervals.

From the results obtained it would appear that the efficiency of phase distribution (as measured by the variance from average flow per port) is a function of throughput. That is, higher air/water flows (and hence a steeper pressure gradient) lead to a better gas/liquid distribution. This observed effect is undoubtedly enhanced by the poorer accuracy of the measuring devices at low flow rates and also by the increasing effect of any fortuitous physical variations between the six gas/liquid collection and separation ports. It is therefore highly probable that the actual distribution is always better than the observed distribution. It should also be noted that the corners of the rig of FIGS. 9 and 10 provide a low resistance fluid path to the left-hand and right-hand bays 403 (as illustrated) for geometrical reasons; this effect will also add to the variance observed. A circular cross section catalyst bed will give better gas/liquid distributions than those observed with a rectangular cross section bed.

These gas/liquid distribution studies show that effective gas and liquid co-current downflow hydrogenation reactions can be achieved without using large excesses of hydrogen containing gases.

TABLE 5

| | Water flow in 30–36 liter/min range | |
|---|---|---|
| Air l/min | Air % av. variance | Water % av. variance |
| 9.8 | 42.9 | 6.8 |
| 10.9 | 19.3 | 3.9 |
| 14.8 | 24.8 | 6.5 |
| 19.7 | 21.9 | 5 |
| 29.4 | 15.6 | 3.6 |
| 39.1 | 14.2 | 10.4 |
| 42.4 | 4.2 | 4.4 |
| 49.5 | 12.7 | 9.3 |

TABLE 6

| | Water flow in 44–46 liter/min range | |
|---|---|---|
| Air l/min | Air % av. variance | Water % av. variance |
| 9.3 | 34.8 | 5.3 |
| 10 | 36.6 | 4.2 |
| 19.2 | 20.8 | 5.9 |

TABLE 6-continued

Water flow in 44-46 liter/min range

| Air l/min | Air % av. variance | Water % av. variance |
|---|---|---|
| 20.2 | 16.8 | 4 |
| 28.5 | 14 | 6 |
| 30 | 11.7 | 4.4 |
| 37.9 | 11.8 | 5.2 |
| 40 | 10.2 | 3.9 |
| 44.9 | 12.3 | 4.5 |
| 47.7 | 9.2 | 4.2 |
| 48.4 | 9.1 | 3.1 |

TABLE 7

Water flow in 53-56 liters/min range

| Air l/min | Air % av. variance | Water % av. variance |
|---|---|---|
| 11.4 | 21.1 | 5.6 |
| 13.1 | 23.4 | 6.5 |
| 20.2 | 13.5 | 5.2 |
| 33.1 | 8.9 | 2.9 |
| 33.3 | 8.4 | 5.4 |
| 43 | 5.6 | 3.4 |
| 43.3 | 5.8 | 3.3 |
| 43.7 | 7.5 | 4.4 |
| 50.3 | 3.8 | 3.6 |
| 59.8 | 7.6 | 3.6 |

We claim:

1. A liquid phase catalytic hydrogenation process in which an organic feedstock is contact with hydrogen in the presence of a solid hydrogenation catalyst under hydrogenation conditions to produce a hydrogenation product, which process comprises:

passing a feed solution of the organic feedstock in an inert diluent therefor downwardly in co-current with a hydrogen-containing gas through a hydrogenation zone containing a bed of a particulate hydrogenation catalyst whose particles substantially all lie in the range of from about 0.5 mm to about 5 mm, maintaining the bed of catalyst particles under temperature and pressure conditions conducive to hydrogenation, recovering from a bottom part of the bed a liquid phase containing the hydrogenation product, controlling the rate of supply of the feed solution to the bed so as to maintain a superficial liquid velocity of the liquid down the bed in the range of from about 1.5 cm/sec to about 5 cm/sec, and controlling the rate of supply of the hydrogen-containing gas to the bed at the chosen rate of supply of feed solution so as to set up a pressure drop across the bed of at least about 0.1 kg/cm² per meter of bed depth, so as to maintain at the top surface of the bed of catalyst particles of flow of hydrogen-containing gas containing from 1.00 to about 1.15 times the stoichiometric quantity of hydrogen theoretically necessary to convert the organic feedstock completely to the hydrogenation product and so as to ensure that all parts of the bed are subjected to forced irrigation with liquid containing entrained bubbles of hydrogen-containing gas.

2. A process according to claim 1, in which the hydrogenation conditions include use of a pressure of from about 1 bar to about 300 bar and of a temperature of from about 40° C. to about 350° C.

3. A process according to claim 1 or claim 2, in which the organic feedstock comprises an aldehyde containing from 2 to about 20 carbon atoms, and in which the hydrogenation product is an alcohol containing from 2 to about 20 carbon atoms.

4. A process according to claim 3, in which the hydrogenation conditions include use of a pressure of from about 5 bar to about 50 bar and of a temperature of from about 90° C. to about 220° C.

5. A process according to claim 1 or claim 2, in which the organic feedstock is an unsaturated hydrocarbon.

6. A process according to any one of claims 1, or 2, in which the superficial liquid velocity down the bed is from about 1.5 cm/sec up to about 3 cm/sec.

7. A process according to any one of claims 1, or 2, in which the hydrogen containing gas contains at least about 90 mole % of hydrogen.

8. A process according to any one of claims 1, or 2, in which the hydrogenation zone is operated under adiabatic conditions and the concentration of organic feedstock in the feed solution is selected to produce an adiabatic temperature rise in passage through the bed of not more than about 30° C.

9. A process according to any one of claims 1, or 2, in which the particles of the particulate hydrogenation catalyst substantially all lie in the range of from about 0.5 mm to about 3 mm.

10. A process according to claim 3, in which the superficial liquid velocity down the bed is from about 1.5 cm/sec up to about 3 cm/sec.

11. A process according to claim 5, in which the superficial liquid velocity down the bed is from about 1.5 cm/sec up to about 3 cm/sec.

12. A process according to claim 3, in which the hydrogen-containing gas contains at least about 90 mole % of hydrogen.

13. A process according to claim 5, in which the hydrogen-containing gas contains at least about 90 mole % of hydrogen.

14. A process according to claim 6, in which the hydrogen-containing gas contains at least about 90 mole % of hydrogen.

15. A process according to claim 3, in which the hydrogenation zone is operated under adiabatic conditions and the concentration of organic feedstock in the feed solution is selected to produce an adiabatic temperature rise in passage through the bed of not more than about 30° C.

16. A process according to claim 5, in which the hydrogenation zone is operated under adiabatic conditions and the concentration of organic feedstock in the feed solution is selected to produce an adiabatic temperature rise in passage through the bed of not more than about 30° C.

17. A process according to claim 6, in which the hydrogenation zone is operated under adiabatic conditions and the concentration of organic feedstock in the feed solution is selected to produce an adiabatic temperature rise in passage through the bed of not more than about 30° C.

18. A process according to claim 7, in which the hydrogenation zone is operated under adiabatic conditions and the concentration of organic feedstock in the feed solution is selected to produce an adiabatic temperature rise in passage through the bed of not more than about 30° C.

19. A process according to claim 3, in which the particles of the particulate hydrogenation catalyst substantially all lie in the range from about 0.5 mm to about 3 mm.

20. A process according to claim 5, in which the particles of the particulate hydrogenation catalyst substantially all lie in the range from about 0.5 mm to about 3 mm.

21. A process according to claim 6, in which the particles of the particulate hydrogenation catalyst substantially all lie in the range from about 0.5 mm to about 3 mm.

22. A process according to claim 7, in which the particles of the particulate hydrogenation catalyst substantially all lie in the range of about 0.5 mm to about 3 mm.

23. A process according to claim 8, in which the particles of the particulate hydrogenation catalyst substantially all lie in the range from about 0.5 mm to about 3 mm.

* * * * *

UNITED STATES PATENT AND TRADEMARK OFFICE
CERTIFICATE OF CORRECTION

PATENT NO. : 5,093,535

DATED : March 3, 1992

INVENTOR(S) : George E. Harrison et al.

It is certified that error appears in the above-identified patent and that said Letters Patent is hereby corrected as shown below:

On the cover page, in the Abstract, line 4,
"contracted" should be --contacted--.

Column 8, line 17, after "applied" insert a
period --.--;
line 32, after "thereof" insert a
period --.--.

Column 15, line 45, "f" should be --force--.

Signed and Sealed this

Nineteenth Day of October, 1993

Attest:

BRUCE LEHMAN

*Attesting Officer*    *Commissioner of Patents and Trademarks*